(12) United States Patent
Zhang et al.

(10) Patent No.: US 11,894,186 B2
(45) Date of Patent: Feb. 6, 2024

(54) PARALLEL MOBILE COIL MECHANISM FOR MAGNETIC MANIPULATION IN LARGE WORKSPACE

(71) Applicant: Multi-Scale Medical Robotics Center Limited, Hong Kong (CN)

(72) Inventors: Li Zhang, Hong Kong (CN); Lidong Yang, Hong Kong (CN); Moqiu Zhang, Hong Kong (CN)

(73) Assignee: Multi-Scale Medical Robotics Center Limited, Hong Kong (CN)

( * ) Notice: Subject to any disclaimer, the term of this patent is extended or adjusted under 35 U.S.C. 154(b) by 271 days.

(21) Appl. No.: 17/350,873

(22) Filed: Jun. 17, 2021

(65) Prior Publication Data

US 2021/0398724 A1    Dec. 23, 2021

Related U.S. Application Data

(60) Provisional application No. 63/040,057, filed on Jun. 17, 2020.

(51) Int. Cl.
    *H01F 7/06*      (2006.01)
    *H01F 7/20*      (2006.01)
    (Continued)

(52) U.S. Cl.
    CPC .............. *H01F 7/064* (2013.01); *A61B 34/30* (2016.02); *A61B 34/73* (2016.02); *H01F 7/20* (2013.01);
    (Continued)

(58) Field of Classification Search
    CPC ... A61B 34/30; A61B 34/73; A61B 2034/731; A61B 2034/735; A61B 2034/2063;
    (Continued)

(56) References Cited

U.S. PATENT DOCUMENTS

6,311,082 B1 * 10/2001 Creighton, IV ....... A61B 34/73
    600/407
6,459,924 B1    10/2002 Creighton, IV et al.
(Continued)

FOREIGN PATENT DOCUMENTS

EP      2 995 240 A1    3/2016

*Primary Examiner* — Kevin J Comber
(74) *Attorney, Agent, or Firm* — Saliwanchik, Lloyd & Eisenschenk

(57) ABSTRACT

A magnetic manipulation system and method for moving and navigating a magnetic device in a body are provided. The system includes a robotic parallel mechanism having at least three electromagnets and at least three electromagnetic coils coupled to the at least three electromagnets, respectively. The electromagnetic coils are actuated to keep the electromagnets in static conditions or move the electromagnets along a desired trajectory, a current control unit supplying currents to the electromagnetic coils which have soft iron cores. The currents supplied by the control unit are configured to generate dynamic magnetic field in the soft iron core's linear region. The current control unit and the robotic parallel mechanism are configured to generate desired dynamic magnetic fields in desired positions within a workspace to control a magnetic device, and a three-dimensional position sensor is configured for performing a close loop control of the robotic parallel mechanism.

10 Claims, 35 Drawing Sheets

(51) Int. Cl.
- *H01F 27/28* (2006.01)
- *A61B 34/00* (2016.01)
- *A61B 34/30* (2016.01)
- *H01F 27/24* (2006.01)

(52) U.S. Cl.
CPC ............ *H01F 27/24* (2013.01); *H01F 27/28* (2013.01); *A61B 2034/733* (2016.02)

(58) Field of Classification Search
CPC ..... A61B 2090/378; H01F 7/064; H01F 7/20; H01F 5/02; H01F 27/24; H01F 27/306; H01F 27/28; H01F 27/2876
USPC ........................................................ 361/160
See application file for complete search history.

(56) References Cited

U.S. PATENT DOCUMENTS

| | | |
|---|---|---|
| 6,975,197 B2 | 12/2005 | Creighton, IV |
| 7,073,513 B2 | 7/2006 | Cha et al. |
| 8,452,377 B2 * | 5/2013 | Reinschke ............ A61B 34/73 600/434 |
| 9,445,711 B2 | 9/2016 | Sitti et al. |
| 10,004,566 B2 | 6/2018 | Park et al. |
| 2012/0281330 A1 * | 11/2012 | Abbott ................... A61B 34/70 361/143 |
| 2014/0066752 A1 | 3/2014 | Shapiro et al. |
| 2015/0230810 A1 | 8/2015 | Creighton et al. |
| 2015/0380140 A1 | 12/2015 | Duan et al. |
| 2016/0143514 A1 | 5/2016 | Mahoney et al. |
| 2017/0150874 A1 | 6/2017 | Kawano et al. |
| 2019/0104994 A1 * | 4/2019 | Valdastri ............ A61B 1/00158 |

* cited by examiner $Pp = [0\ 0\ 50]^T$

PARALLEL MOBILE COIL MECHANISM FOR MAGNETIC MANIPULATION IN LARGE WORKSPACE

CROSS-REFERENCE TO RELATED APPLICATION

This application claims the benefit of U.S. Provisional Application Ser. No. 63/040,057, filed Jun. 17, 2020, which is hereby incorporated by reference in its entirety including any tables, figures, or drawings.

BACKGROUND OF THE INVENTION

Untethered small-scale magnetically actuated devices have been an active and attracted research field during last two decades. These devices typically consist of some forms of mechatronic or micro electromechanical systems (MEMS) devices with a rigidly attached magnetic body on which magnetic forces and torques are applied by an external field. Their great potential in minimally invasive surgery/medicine has been widely noticed due to the intrinsic advantages of magnetic field, such as high safety to living organisms and good controllability. Compare to traditional endoscopy, using magnetic capsule endoscopes in diagnosing diseases in the gastrointestinal tract reduces the examination time and retention rate. Actively controlled capsule endoscopy would also allow the examination of the entire gastrointestinal (GI) tract. For vascular diseases, endovascular interventions using magnetic catheters have advantages over traditional manual techniques in terms of accuracy and surgical or diagnostic duration.

To actuate and control the aforementioned magnetic medical devices, various magnetic manipulation systems generating magnetic torque and/or magnetic force are proposed. Some approaches utilize magnetic forces for pulling while others apply torques generated by rotating magnetic fields to roll on a surface, travel through a fluid, crawl through a lumen via helical propulsion, or screw through soft tissues. These systems adopt either electromagnetic coils or permanent magnets for field generation. Using multiple stationary electromagnetic coils, systems with different configurations have been developed for magnetic manipulation. Helmholtz or near-Helmholtz coils and their combinations with Maxwell coils are most commonly used. Towards specific applications, researchers have developed custom stationary magnetic manipulation systems for both minimally invasive operation and micro robotic research. However, when facing a requirement of a large workspace (for example, with the human body size), the limitations of this type of design using stationary coils emerge. The large coil size and heavy weight may lead to higher complexity on the structural design and fabrication. Increased inductance of the enlarged coil limits the control bandwidth of the effective magnetic field.

Alternative methods employ permanent magnets to create dynamic magnetic fields. However, due to large inertia and limited motion range of the permanent magnets, this kind of system has low control bandwidth. For tackling the problems of scalability and control bandwidth, systems with mobile permanent magnets provide a solution. Owning to the strong magnetic field and compact size, a single permanent magnet can be carried by a human hand or a serial robotic manipulator to reach a large workspace. Its magnetic field is controlled by adjusting the position and pose of the magnet. Considering that control of the magnetic field generated by permanent magnets is a challenging task, there may be safety concerns in applications since the field of permanent magnets cannot be switched off.

Although electromagnetic coils and permanent magnets generate equivalent magnetic fields, coils have often been the preferred choice due to their abilities to easily control the field by regulating the coil currents and to completely turn off the field. Concepts of magnetic manipulation using several mobile coils were proposed. The advantages of this type of system are revealed compared to stationary coil systems and permanent magnet systems. However, up to now, only one-dimensional (1D) rotation and planar motion of coils were realized. Two main challenges hinder the realization of three-dimensional (3D) motion of multiple coils. On one hand, large sizes and weights of the coils, which are utilized to generate a strong magnetic field, brings in the design complexity of the positioning mechanism. On the other hand, position and pose variations of multiple coils lead to challenges in computing the resulting composite field in real time.

BRIEF SUMMARY OF THE INVENTION

There continues to be a need in the art for improved designs and techniques for a system for manipulating and guiding small-scale magnetically actuated devices for clinical applications.

Embodiments of the subject invention pertain to a magnetic manipulation system having mobile coils for moving and navigating a magnetic device in a body.

According to an embodiment of the subject invention, the magnetic manipulation system comprises a robotic parallel mechanism comprising at least three electromagnets and at least three electromagnetic coils coupled to the at least three electromagnets, respectively, wherein the electromagnetic coils are configured be actuated to keep the electromagnets in static conditions or move the electromagnets along a desired trajectory; a current control unit supplying currents to the electromagnetic coils, the electromagnetic coils having soft iron cores, wherein the currents supplied by the control unit is configured to generate dynamic magnetic field in the soft iron core's linear region, wherein the current control unit and a robotic parallel mechanism are configured to generate desired dynamic magnetic fields in desired positions within a workspace to control a magnetic device; and a three-dimensional (3D) position sensor is configured for performing a close loop control of the robotic parallel mechanism. The magnetic manipulation system may further comprise a coil-end joint plate, actuation units and structural linkages that connect the coil-end joint plate to the robotic parallel mechanism. The coil-end joint plate has a plurality of sides corresponding to a plurality of branches of each electromagnetic coil; wherein instruments are mounted on the coil-end joint plate and the coil-end joint plate is connected to the lower end of every electromagnetic coil. The robotic parallel mechanism is an actuation mechanism of K branches including linear actuation mechanisms and rotational actuation mechanisms, wherein K is an integer greater than zero, and wherein the rotational actuation mechanisms include motors and gears, motors and belts, or motors and linkages; and wherein the linear actuation mechanisms include ball screw tables, sliding track and pneumatic actuation. The robotic parallel mechanism is made of low magnetic permittivity materials including aluminum and 304 steel. A position of a center of the coil-end joint plate has a deterministic relationship with actuator positions of the robotic parallel mechanism while an orientation of the coil-end joint plate is constrained by the robotic parallel mechanisms to be invariant. The coil-end joint plate is configured to install one or more instruments selected from 3D ultrasonic probes, 3D magnetic sensors or stereo cameras, the 3D ultrasonic probes, the 3D magnetic sensors and the stereo cameras being modulated and interchangeable. A 3D location method is configured to conduct close loop control of a plurality of magnetic objects, and wherein the 3D location method includes one or more selected from ultrasonic imaging, magnetic localization, and vision-based localization method, depending on the instruments installed on the coil-end plate. The electromagnetic coils are connected to the coil-end joint plate by universal joints, and wherein the electromagnetic coils move and are aligned with the structural linkages. The magnetic manipulation system can further comprise an isolation plate attached to the coil-end joint plate for controlling a distance between the magnetic manipulation system and the body that includes magnetically controlled objects and integrates distance sensors and temperature sensors to inhibit body collision and overheating.

In another embodiment, a method of a magnetic manipulation system having mobile electromagnetic coils for moving and navigating a magnetic device in a body is provided. The method determines parameters of the magnetic manipulation system to keep the magnetic manipulation system as compact as possible and inhibit any singularities with respect to both kinematics and field generation. The method can comprise analyzing a workspace of the magnetic manipulation system; determining spatial relationships between coil branches of the magnetic manipulation system and actuation mechanisms of the coil branches; and determining optimal link length of the coil branches. The method can further comprise optimizing for deriving the optimal link length, wherein performance metrics for motion actuation and field generation are evaluated based on a condition number of the performance metrics. The workspace is axis-symmetric and a bottom center of the workspace is located on a symmetry axis of the workspace. The spatial relationship between the coil branches and the moving trajectories of the coil branches is delimited by the singularities and physical constraints of the magnetic manipulation system. The link length is optimized based on minimum radius of the magnetic manipulation system and whether there is enough space for hardware implementation. The method can further comprise providing a framework for calculating and controlling field generation of the coil branches of the magnetic manipulation system, wherein the framework includes a field map of a one or more of the coil branches, inverse kinematics of the coil branches and field computation and control by dynamic coordinate transformation. The method can further comprise generating and calibrating a unit map of one of the coil branches; wherein the coil branches each has a length-to-diameter ratio greater than 3, a field map domain greater than twice of a diameter of the corresponding coil branch and a distance between the corresponding coil branch and the field map domain smaller than one half of a length of the corresponding coil branch; wherein a neural network is utilized to calibrate finite element data created by a simulation of the field map domain of the corresponding coil branch; wherein real magnetic field vectors which are experimentally measured at data points are based on to calibrate a 3D magnetic field map and the magnetic field gradient. The method can further comprise providing currents to the coil branches for generating desired magnetic field, which comprises deriving the inverse kinematics of the coil branches and field computing and controlling by the dynamic coordinate transformation; wherein the magnetic field calculation and the field superposition of the coil branches is performed by the dynamic coordinate transformation and a unit map of one of coil branches; wherein the resulting magnetic field vectors and the gradient matrices connect the currents the coil branches that is controllable to a desired magnetic field.

In certain embodiment, an interchangeable coil assembly can comprise a core, a coil frame, and a coil. The coil frame decouples the coil and the core, and either of the part is changed when the other one fails, and different core tips are configured to be inserted in the coil frame to meet magnetic field requirements. The interchangeable coil assembly can further comprise a cooling unit for controlling temperature of the coil, and the temperature control unit monitoring the coil temperature through thermal sensors and regulating the heat exchange rate to keep the coil in a suitable working condition and elongate continuous working time of the interchangeable coil assembly.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

FIGS. 11A-11F shows alternative actuation systems and methods for different applications, wherein FIGS. 11A-11C show alternative actuation systems and methods with various rotational joints and FIGS. 11A-11C show alternative actuation systems and methods with various linear actuations, according to an embodiment of the subject invention.

DETAILED DISCLOSURE OF THE INVENTION

The presented invention relates to a magnetic manipulation and navigation system comprising at least three electromagnetic coils for moving and navigating magnetic devices in or through a body of a living creature. Such a body may have a cavity comprising liquid or soft tissues and a magnetic device to be displaced inside the cavity. Electromagnetic coils are structured in a parallel mechanism and can move to predetermined positions in the vicinity of the body.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not prelude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention pertains. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

When the term "about" is used herein, in conjunction with a numerical value, it is understood that the value can be in a range of 90% of the value to 110% of the value, i.e. the value can be +/−10% of the stated value. For example, "about 1 kg" means from 0.90 kg to 1.1 kg.

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Figure 1:
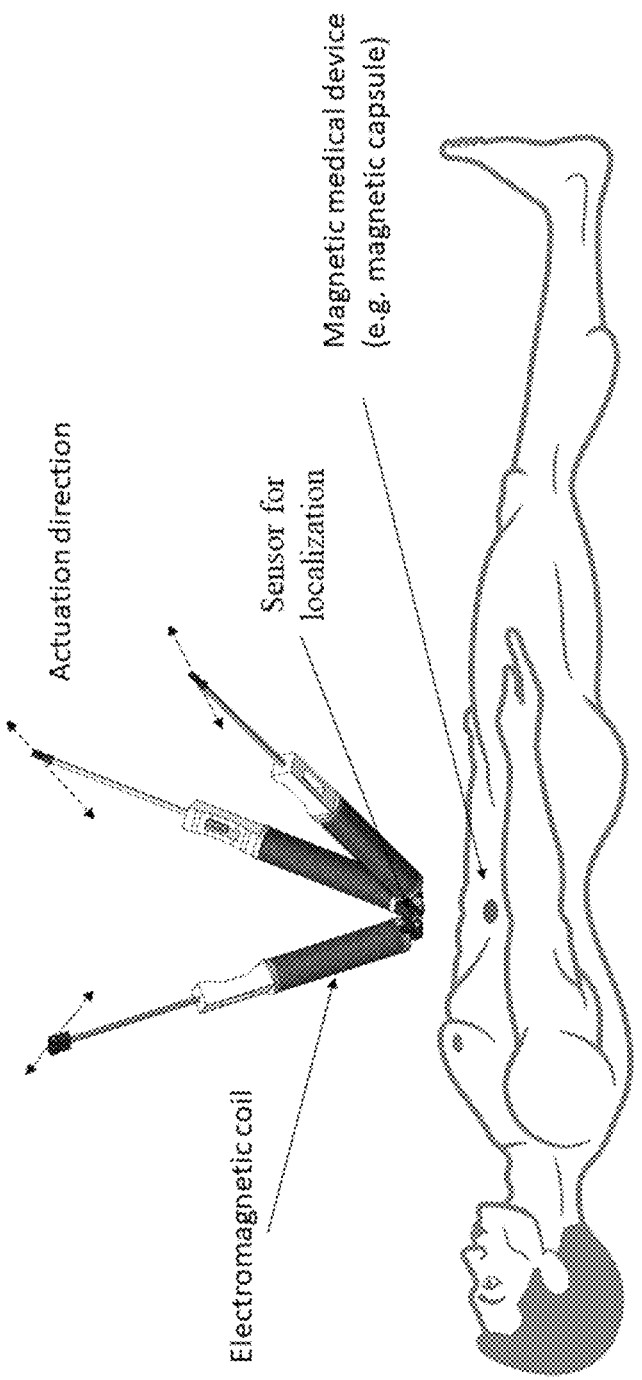
FIG. 1 is a schematic representation illustrating a magnetic manipulation system having mobile parallel electromagnetic coils, according to an embodiment of the subject invention.

Referring to FIG. 1, a magnetic manipulation system comprises a plurality of, for example three, mobile electromagnetic coils and a robotic parallel mechanism for controlling one or more magnetic devices navigating the body. The body can be viewed as a cavity comprising workspace filled with liquid or air. The plurality of, for example three, mobile electromagnetic coils is actuated by parallel mechanisms to realize a large effective 3-dimensional workspace of the body.

Desired magnetic fields for manipulation of the magnetic devices are achieved by controlling electrical currents of the plurality of electromagnetic coils. The manipulation is realized by localization of the magnetic devices using sensors so that the energy consumption and heat generation are reduced.

In one embodiment, an implementation of high-resolution localization sensors is realized for easy eye-in-hand configuration. The employment of the plurality of electromagnetic coils makes it safe for the human body since the magnetic fields can be easily switched off. The magnetic devices such as magnetic capsules are positioned in the body and controlled by the magnetic field generated by the mobile electromagnetic coils.

In one embodiment, the magnetic manipulation system can comprise any number of electromagnetic coils and a shape of the coil-end joint plate may vary. By performing the actuation method of the magnetic manipulation system, the electromagnetic coils can move to desired locations within the working space of the body.

Large workspace is ensured by the mobility of the parallel-robotic structure. The magnetic manipulation system is highly accessible because the mobile electromagnetic coils only take a part of the workspace. When the system is turned on, the robotic parallel structure can either stay static to keep the electromagnetic coils in a predetermined position or move along a desired trajectory. The current supply unit, working together with the parallel coil actuation method, controls the current of the coils to generate desired dynamic magnetic field.

In one embodiment, the magnetic manipulation system comprises K electromagnetic coils, each of which is actuated by a linear actuator that moves on a fixed track as shown in FIG. 1, wherein K is a positive integer value. The other ends of the electromagnetic coils are symmetrically attached to the coil-end plate via connections such as ball joints. With this configuration and the assumption that orientation of the coil-end plate is constrained to be invariant, the position of the center of the coil end plate ($p_P^G \in \mathbb{R}$) has a unique deterministic relationship with the actuator positions ($q=[q_1\ q_2\ \ldots\ q_K]^T \in \mathbb{R}^K$) shown by Equation (1):

$$p_P^G = \mathcal{F}(q) \tag{1}$$

where $\{\mathcal{G}\}$ denotes the global coordinate frame.

It is noted that the inverse of equation (1), i.e. $q=\mathcal{F}^{-1}(p_P^G)$, exists, which represents the inverse kinematics of the parallel method. The position of a working point ($P_w \in \mathbb{R}^3$) expressed in the local reference frame—$\{\mathcal{C}_k\}$ of the k-th coil is $p_w^{C_k} \in \mathbb{R}^3$, and the coordinate transformation is defined by Equation (2):

$$p_w^{C_k} = {}^{C_k}T_\mathcal{G}(p_w^\mathcal{G}, p_P^\mathcal{G}) \tag{2}$$

Due to the varied position and pose of the coil relative to the coil-end plate and nonlinearity of $\mathcal{F}(q)$, ${}^{C_k}T_\mathcal{G}(p_w^\mathcal{G}, p_P^\mathcal{G})$ is a series of nonlinear transformation functions.

When the $k^{th}$ coil with a soft iron core is operated in its linear range, its magnetic field ($\mathbf{h}_k^{C_k} \in \mathbb{R}^3$, unit: mT) and gradient matrix ($\mathbf{G}_k^{C_k} \in \mathbb{R}^{3\times3}$, unit: mT/m) at $\mathbf{p}_W^{C_k}$ depend linearly on the coil current ($i_k$) and are given by Equation (3):

$$\begin{cases} h_k^{C_k}(p_W^{C_k}) = i_k \cdot \overline{h}_k^{C_k}(p_W^{C_k}) = i_k \cdot \overline{\mathcal{M}}_k^{C_k}(p_W^{C_k}) \\ G_k^{C_k}(p_W^{C_k}) = i_k \cdot \overline{G}_k^{C_k}(p_W^{C_k}) = i_k \cdot \left( \frac{\partial \mathcal{M}_k^{C_k}(p_W^{C_k})}{\partial x^{C_k}} \frac{\partial \mathcal{M}_k^{C_k}(p_W^{C_k})}{\partial y^{C_k}} \frac{\partial \mathcal{M}_k^{C_k}(p_W^{C_k})}{\partial z^{C_k}} \right)^T \end{cases} \quad (3)$$

where $\overline{\mathcal{M}}_k^{C_k}(\cdot)$ stands for the unit field map of the $k^{th}$ coil at its local frame. After coordinate transformation, the magnetic field in the global coordinate frame is obtained by Equation (4):

$$\mathbf{h}_k^{\mathcal{G}}(\mathbf{p}_W^{\mathcal{G}}) = {}^{\mathcal{G}}\mathbf{R}_{C_k}(\mathbf{p}_W^{C_k}, \mathbf{p}_P^{\mathcal{G}}) \cdot \mathbf{h}_k^{C_k}(\mathbf{p}_W^{C_k}) \quad (4)$$

where ${}^{\mathcal{G}}\mathbf{R}_{C_k}(\mathbf{p}_W^{C_k}, \mathbf{p}_P^{\mathcal{G}}) \in \mathbb{R}^{3\times3}$ is the corresponding rotation matrix for the k-th coil.

There are two types of control methods for the magnetic devices: a magnetic torque control method and a magnetic force control method. For devices that are controlled by the magnetic torque method (for example, microrobots moving in liquid that align with orientation of magnetic field), the device control method is essentially based on a magnetic field control method. According to the superposition property of magnetic fields and assuming that the magnetic field of a coil is in a linear relationship with the coil current, the total field at $p_w^{\mathcal{G}}$ is computed by Equation (5):

$$\mathbf{h}^{\mathcal{G}}(\mathbf{p}_W^{\mathcal{G}}) = [\mathbf{h}_1^{\mathcal{G}}(\mathbf{p}_W^{\mathcal{G}}) \, \mathbf{h}_2^{\mathcal{G}}(\mathbf{p}_W^{\mathcal{G}}) \, \ldots \, \mathbf{h}_k^{\mathcal{G}}(\mathbf{p}_W^{\mathcal{G}})] \cdot i = \overline{H} \cdot i \quad (5)$$

where $i = [i_1 \, i_2 \, \ldots \, i_K]^K \in \mathbb{R}^k$ is the vector of coil currents. If a desired field is given and H does not have singularity, the exact required coil currents can be obtained by Equation (6):

$$i = \overline{H}^\dagger \cdot \mathbf{h}^{\mathcal{G}}(\mathbf{p}_W^{\mathcal{G}}) \quad (6)$$

where $\overline{H}^\dagger$ represents the general inverse of $\overline{H}$.

Unlike the torque control method, the force control method requires a different computation process because the gradient matrix is non-rotational. To solve this problem, the unit magnetic forces at the local frames are first calculated by Equation (7):

$$\overline{f}^{C_k}(p_W^{C_k}, m^{\mathcal{G}}) = \overline{G}_k^{C_k}(p_W^{C_k}) \cdot m^{C_k} = \overline{G}_k^{\mathcal{G}}(p_W^{C_k}) \cdot {}^{C_k}R_{\mathcal{G}}(p_W^{\mathcal{G}}, p_P^{\mathcal{G}}) \cdot m^{\mathcal{G}} \quad (7)$$

where $m^{\mathcal{G}} \in \mathbb{R}^3$ is the magnetic moment of the controlled magnetic device, and ${}^{C_k}R_{\mathcal{G}}(\mathbf{p}_W^{\mathcal{G}}, \mathbf{p}_P^{\mathcal{G}}) = {}^{\mathcal{G}}R_{C_k}^{-1}(\mathbf{p}_W^{\mathcal{G}}, \mathbf{p}_P^{\mathcal{G}})$. Then, the unit magnetic forces are transformed to the global coordinate frame by Equation (8):

$$\overline{f}_k^{\mathcal{G}}(\mathbf{p}_W^{C_k}, m^{\mathcal{G}}) = {}^{\mathcal{G}}R_{C_k}(\mathbf{p}_W^{C_k}, \mathbf{p}_P^{\mathcal{G}}) \cdot \overline{f}^{C_k}(\mathbf{p}_W^{C_k}, m^{\mathcal{G}}) \quad (8)$$

According to the superposition principle, the total magnetic force at $p_w^{\mathcal{G}}$ is computed by Equation (9):

$$f^{\mathcal{G}}(\mathbf{p}_W^{C_k}, m^{\mathcal{G}}) = [\overline{f}_1^{\mathcal{G}}(\mathbf{p}_W^{C_k}, m^{\mathcal{G}}) \, \ldots \, \overline{f}_k^{\mathcal{G}}(\mathbf{p}_W^{C_k}, m^{\mathcal{G}})] \cdot i = \overline{F} \cdot i \quad (9)$$

Finally, if a desired force is given and $\overline{F}$ does not have singularity, the exact required coil currents can be obtained by Equation (10)

$$i = \overline{F}^\dagger \cdot f^{\mathcal{G}}(\mathbf{p}_W^{C_k}, m^{\mathcal{G}}) \quad (10)$$

Figure 2:
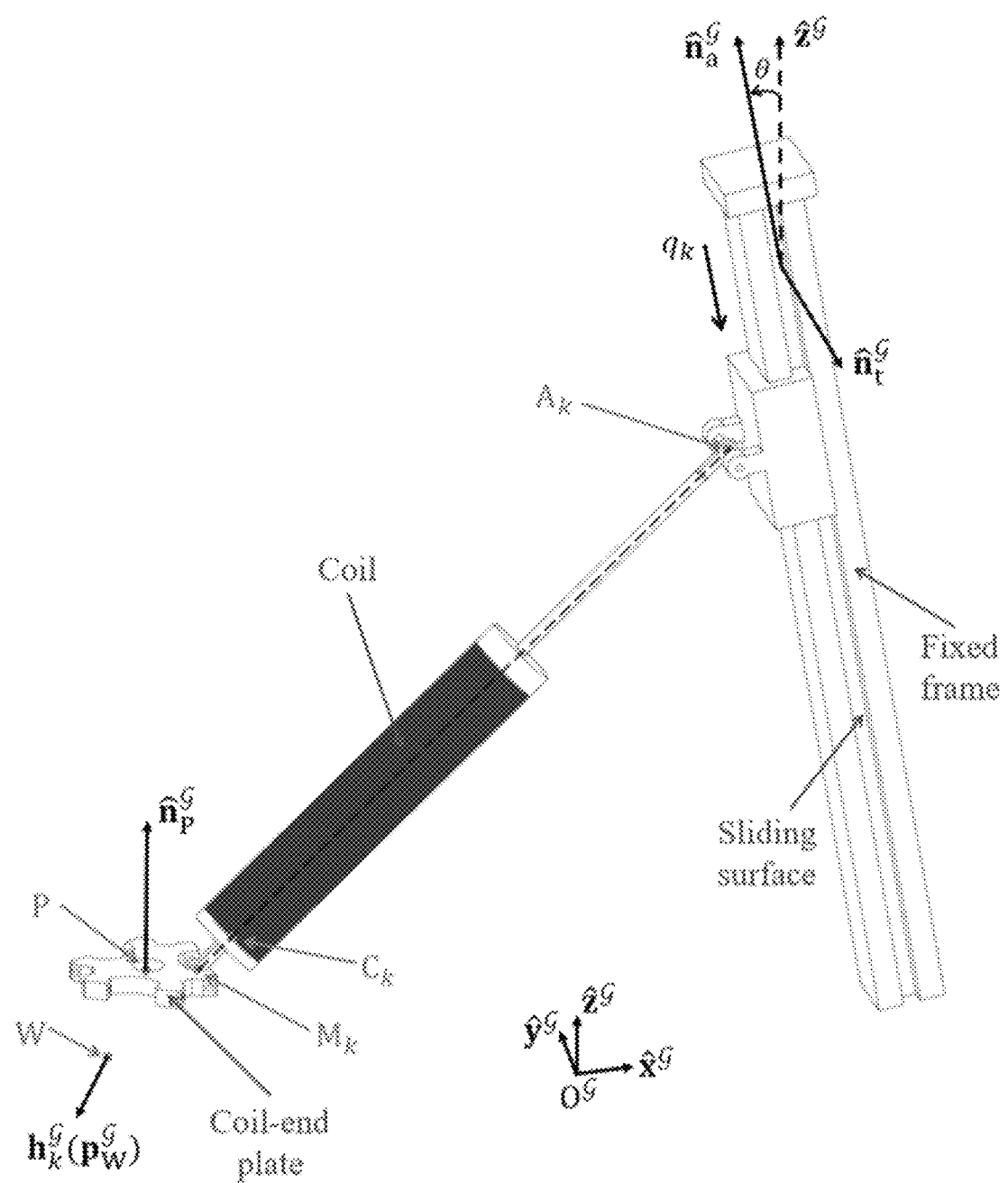
FIG. 2 is a geometric representation of one branch of the mobile parallel coil mechanism, according to an embodiment of the subject invention.

FIG. 2 is a geometric representation of one branch of the parallel-mobile-coil mechanism. The parallel mobile coil comprises K branches having a rotationally symmetric distribution around $\hat{z}^{\mathcal{G}}$. Accordingly, the instrument connected to the parallel mobile coil has K sides to locate the robotic parallel links and the coils.

With two constraints on the mechanical design that the normal vector of the coil end plate—$\hat{n}_P^{\mathcal{G}}$, is in parallel to $\hat{z}^{\mathcal{G}}$ and the normal vector of the sliding surface of the linear actuator—$\hat{n}_l^{\mathcal{G}}$ is perpendicular to $\hat{z}^{\mathcal{G}}$.

In one embodiment, the magnetic manipulation system of FIG. 1 has three branches, wherein the parallel kinematics can be derived. Nevertheless, the value of θ can be flexibly chosen for specific application scenarios. The type of parallel actuated mechanism of FIG. 2 can also be rotational mechanisms or any other parallel mechanism as long as the actuators fulfill the requirements of the parallel mechanism.

All electromagnetic coils comprise soft iron cores and are connected to coil-end plate by universal joints as shown in FIG. 1. Triangular-shaped instrument plate which corresponds to the number of coils can be used. Universal joints may also be ball joints or other types of two degree of freedom (DOF) joints that allow the parallel movement of the robotic structure.

The inverse kinematics that is necessary for the closed-loop control of the parallel-mobile-coil mechanism is derived as below. Coordinates of all the points are computed with respect to the global coordinate frame { $\mathbf{O}^{\mathcal{G}} - \hat{x}^{\mathcal{G}} \hat{y}^{\mathcal{G}} \hat{z}^{\mathcal{G}}$ }. As shown in FIG. 2, points P and W denote the positions of the coil-end plate and the magnetic device, respectively. Their coordinates are expressed by $\mathbf{p}_P^{\mathcal{G}} = [x_P, y_P, z_P]^T$ and $\mathbf{p}_W^{\mathcal{G}} = [x_W \, y_W \, z_W]^T \cdot q_k$ stands for the position of the $k^{th}$ (k=1, 2, ..., K) linear actuator moving from a top home position. By the mechanism design, coordinates of $M_k$ are calculated by Equation (11):

$$p_{M_k}^{\mathcal{G}} = \begin{bmatrix} x_{M_k} \\ y_{M_k} \\ z_{M_k} \end{bmatrix} = \begin{bmatrix} x_P + L_{MP}\cos(\alpha_k) \\ y_P + L_{MP}\sin(\alpha_k) \\ z_P \end{bmatrix} \quad (11)$$

where $L_{MP}$ is a constant length between point P and point $M_k$, and $\alpha_k$ is defined by Equation (12):

$$\alpha_k = \frac{360°}{K}(k-1) \quad (12)$$

Similarly, coordinates of $A_k$ are obtained by Equation (13):

$$p_{A_k}^{\mathcal{G}} = \begin{bmatrix} x_{A_k} \\ y_{A_k} \\ z_{A_k} \end{bmatrix} = \begin{bmatrix} (L_h + q_k\sin(\theta))\cos(\alpha_k) \\ (L_h + q_k\sin(\theta))\sin(\alpha_k) \\ L_V - q_k\cos(\theta) \end{bmatrix} \quad (13)$$

where $L_h$ and $L_V$ stand for the horizontal distance and vertical distance between $\mathbf{O}^{\mathcal{G}}$ and $A_k$ when $q_k=0$, respectively. From the mechanical constraint, $\|p_{A_k}^G - p_{M_k}^G\|$ is a constant, as shown in Equation (14):

$$\|p_{A_k}^G - p_{M_k}^G\| - L_{AM} = 0 \tag{14}$$

By Eq. (10)-(13), the inverse kinematics of the parallel-mobile-coil mechanism is obtained by Equation (15):

$$q_k = \mathcal{F}^{-1}(p_P^G) = \begin{cases} C_1 - \sqrt{C_1^2 - C_2}, & 0° \le \theta \le 45° \\ C_1 + \sqrt{C_1^2 - C_2}, & 45° \le \theta \le 90° \end{cases} \tag{15}$$

Where $$\begin{cases} C_1 = (x_P\cos\alpha_k + y_P\sin\alpha_k - L_h + L_{MP})\sin\theta + \\ \quad (L_V - z_P)\cos\theta \\ C_2 = x_P^2 + y_P^2 + (z_P - L_V)^2 + (L_h - L_{MP})^2 - L_{AM}^2 - \\ \quad 2(L_h - L_{MP})(x_P\cos\alpha_k + y_P\sin\alpha_k) \end{cases} \tag{16}$$

With the inverse kinematics, the actuators' movements can be controlled to actuate the coil-end plate to the desired location $p_{P_d}^G$.

Due to the variation of the coil positions and poses, field and force computations for every coil in the local frames and the field and force superpositions of multiple coils in the global frame require dynamic coordinate transformations: $^{C_k}T_G(p_W^G, p_P^G)$ transforms the global position of the working point to its position in the local coordinate frame of the $k^{th}$ coil and $^G R_{C_k}(p_W^{C_k}, p_P^G)$ transforms the magnetic field of $k^{th}$ coil in its local coordinate frame to the global coordinate frame for the field superposition. Moreover, $^{C_k}R_G(p_W^G, p_P^G)$ transforms the magnetic moment of the device in the global frame to the corresponding magnetic moment in the local frame of the $k^{th}$ coil for force computation.

Figure 3A:
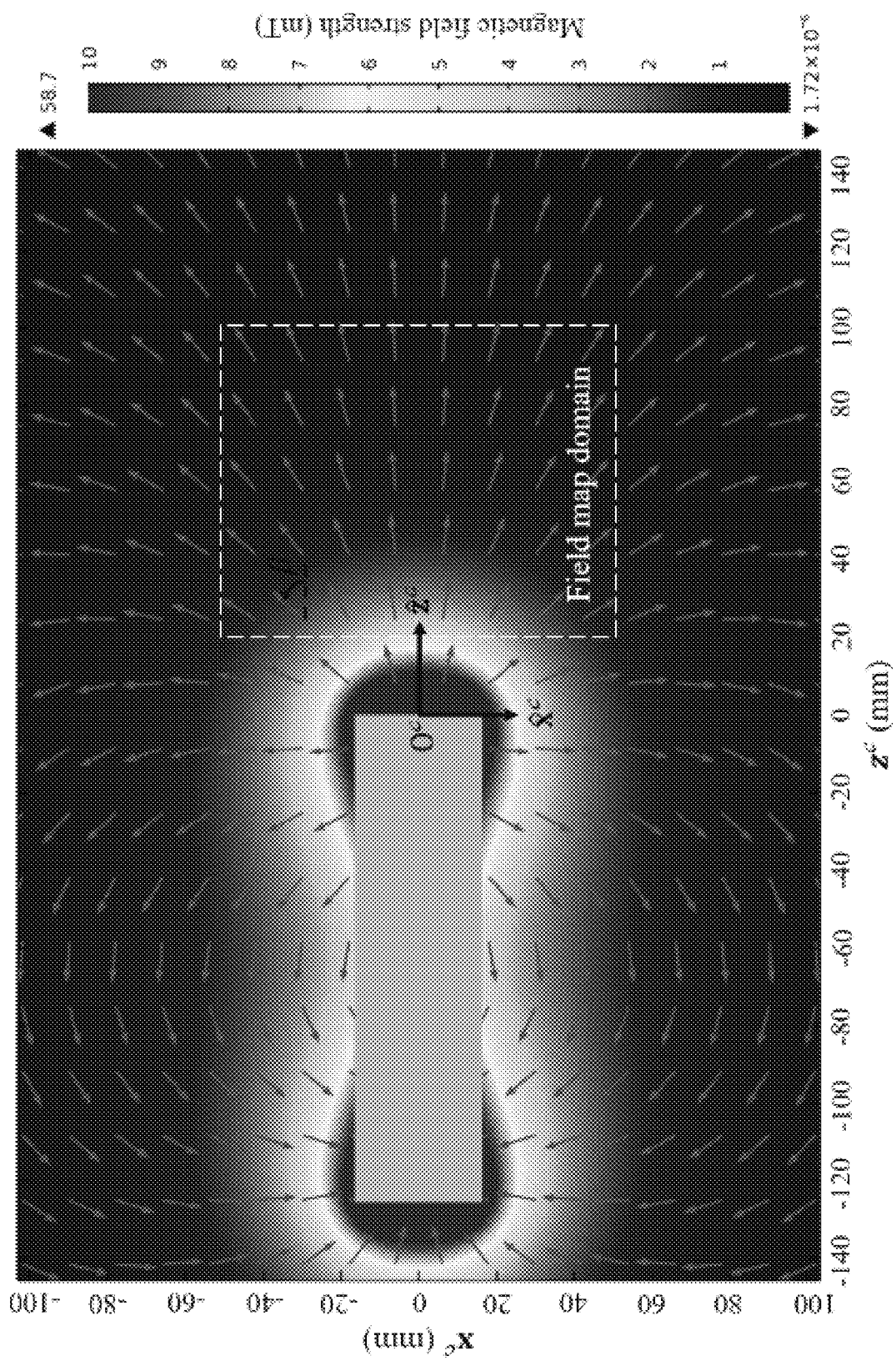
FIGS. 3A-3B show unit field maps of the mobile parallel coils and calibration results of the mobile parallel coils, respectively, according to an embodiment of the subject invention.
Figure 3B:
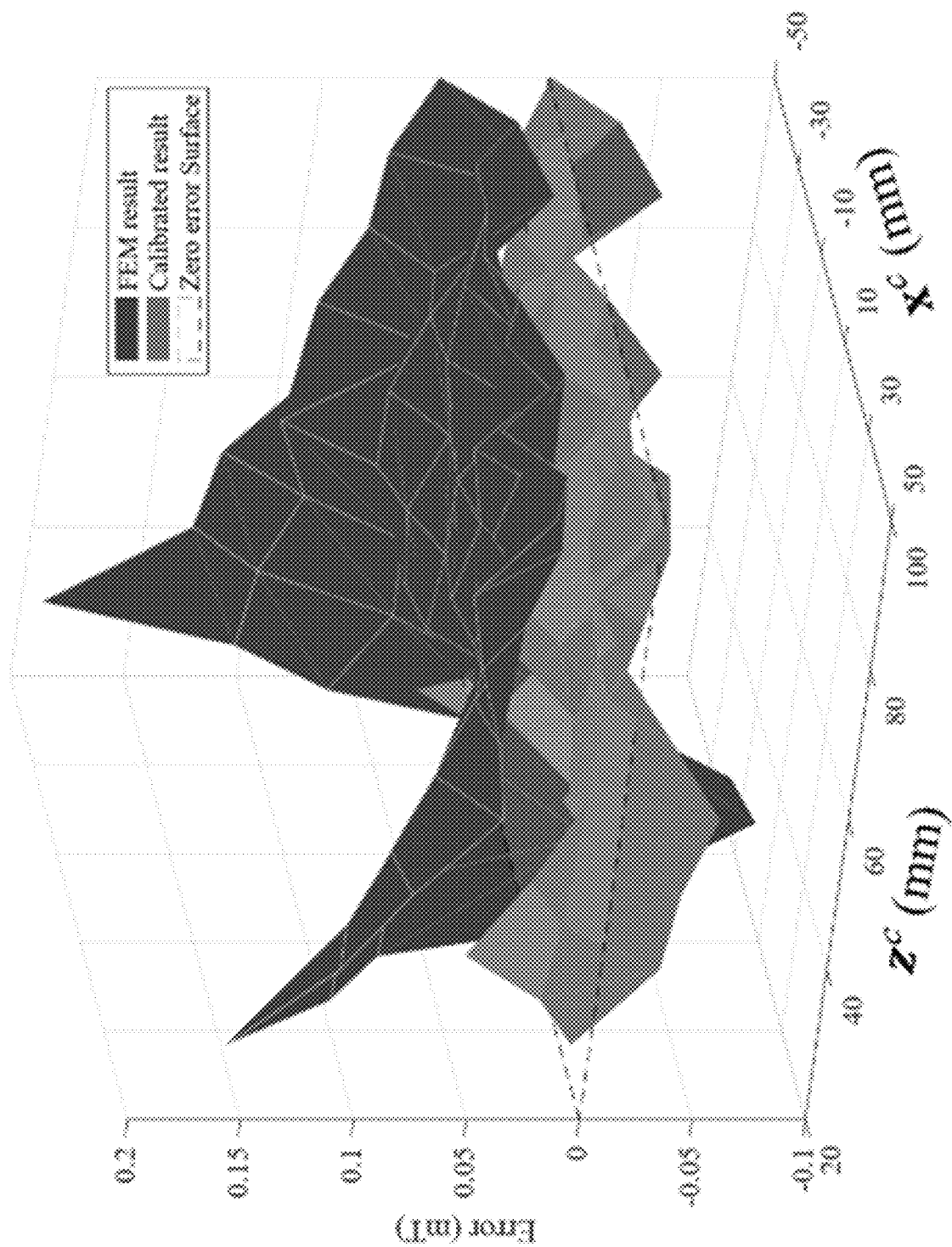

In the global coordinate frame, for the $k^{th}$ coil, the origin $O^{C_k}$ of its local frame coincides with point $C_k$ (as shown in FIG. 2 and FIGS. 3A-3B). The coordinate of $C_k$ is obtained by Equation (17):

$$p_{C_k}^G = \begin{bmatrix} x_{C_k} \\ y_{C_k} \\ z_{C_k} \end{bmatrix} = p_A^G + \frac{L_{AC}}{L_{AM}}(p_{M_k}^G - p_{A_k}^G) \tag{17}$$

where $L_{AC}$ and $L_{AM}$ are constant lengths between $A_k$ and $C_k$ and between $A_k$ and $M_k$, respectively. $p_{AC_k}^G$ denotes the vector from point $A_k$ to point $C_k$, as shown in Equation (18):

$$p_{AC_k}^G = p_{C_k}^G - p_{A_k}^G \tag{18}$$

Since vectors $p_{AC_k}^G$, $p_{CW_k}^G$ and $\bar{h}_k^G(p_W^G)$ are coplanar, the following function holds as shown in Equation (19):

$$| p_{AC_k}^G \; p_{CW_k}^G \; \bar{h}_k^G(p_W^G) | = 0 \tag{19}$$

where $p_{CW_k}^G$ is defined by the same way as $p_{AC_k}^G$, and $|\cdot|$ stands for the determinant operation. To simplify the computation, the local frame $\{C_k\}$ is uniquely determined by two conditions: 1) its $\hat{x}^{C_k}\hat{z}^{C_k}$ plane coincides with the plane expanded by the three vectors in Equation (19); 2) its $\hat{x}^{C_k}$ direction is chosen such that $x_W^{C_k}$ is always greater than or equal to 0. Based on the two conditions, in the local frame of the $k^{th}$ coil, the coordinates of W read as shown in Equations (20)-(22):

$$z_W^{C_k} = \frac{(p_{AC_k}^G)^T \cdot p_{CW_k}^G}{\|p_{AC_k}^G\|} \tag{20}$$

$$y_W^{C_k} = 0 \tag{21}$$

$$x_W^{C_k} = \sqrt{\|p_{CW_k}^G\|^2 - (z_W^{C_k})^2} \tag{22}$$

Next, the coordinates of W are transformed to the local frames of every coil, that is, $p_W^{C_k} = T_k(p_W^G, p_P^G)$ is obtained. Then, by utilizing the established field map of a single coil, Equation (23) is obtained:

$$\bar{h}_k^{C_k}(p_W^{C_k}) = [\bar{h}_{kx}^{C_k} \; \bar{h}_{ky}^{C_k} \; \bar{h}_{kz}^{C_k}]^T = \begin{bmatrix} \Phi_{norm}(x_W^{C_k}, z_W^{C_k}) \cdot \sin(\Phi_\beta(x_W^{C_k}, z_W^{C_k})) \\ 0 \\ \Phi_{norm}(x_W^{C_k}, z_W^{C_k}) \cdot \cos(\Phi_\beta(x_W^{C_k}, z_W^{C_k})) \end{bmatrix} \tag{23}$$

The unit gradient matrix at coil local frames also can be obtained by substituting $p_W^{C_k}$ into the unit map of gradient matrices. Simplified by the cylindrical coil and the establishment method of the local frames, the unit gradient matrix becomes Equation (24):

$$\bar{G}_k^{C_k}(p_W^{C_k}) = \begin{bmatrix} \dfrac{\partial \bar{M}_x^{C_k}(p_W^{C_k})}{\partial x^{C_k}} & 0 & \dfrac{\partial \bar{M}_x^{C_k}(p_W^{C_k})}{\partial z^{C_k}} \\ 0 & \dfrac{\partial \bar{M}_y^{C_k}(p_W^{C_k})}{\partial y^{C_k}} & 0 \\ \dfrac{\partial \bar{M}_x^{C_k}(p_W^{C_k})}{\partial z^{C_k}} & 0 & \dfrac{\partial \bar{M}_z^{C_k}(p_W^{C_k})}{\partial z^{C_k}} \end{bmatrix} \tag{24}$$

where $\dfrac{\partial \bar{M}_z^{C_k}(p_W^{C_k})}{\partial z^{C_k}} = -\left(\dfrac{\partial \bar{M}_y^{C_k}(p_W^{C_k})}{\partial y^{C_k}} + \dfrac{\partial \bar{M}_x^{C_k}(p_W^{C_k})}{\partial x^{C_k}}\right)$.

To transform the obtained magnetic field and field gradient matrix to the global frame for superposition calculation, the rotation matrix $^G R_{C_k}(p_W^{C_k}, p_P^G)$ is derived. For this purpose, the following relationship as shown in Equation (25) is utilized:

$$[\hat{x}_{C_k}^G \; \hat{y}_{C_k}^G \; \hat{z}_{C_k}^G] = {}^G R_{C_k}(p_W^{C_k}, p_P^G) \cdot [\hat{x}^{C_k} \hat{y}^{C_k} \hat{z}^{C_k}] \tag{25}$$

where $\hat{x}_{C_k}^G$ is the global-frame coordinate of the x axis of the local frame of the k-th coil, then $$^G R_{C_k}(p_W^{C_k}, p_P^G) = [\hat{x}_{C_k}^G \; \hat{y}_{C_k}^G \; \hat{z}_{C_k}^G] \cdot [\hat{x}^{C_k} \hat{y}^{C_k} \hat{z}^{C_k}]^{-1} \tag{26}$$

Since $$[\hat{x}^{C_k} \; \hat{y}^{C_k} \; \hat{z}^{C_k}] = \begin{bmatrix} 1 & 0 & 0 \\ 0 & 1 & 0 \\ 0 & 0 & 1 \end{bmatrix} \tag{27}$$

thus, $$^G R_{C_k}(p_W^{C_k}, p_P^G) = [\hat{x}_{C_k}^G \; \hat{y}_{C_k}^G \; \hat{z}_{C_k}^G] \tag{28}$$

where $\hat{z}_{C_k}^G, \hat{x}_{C_k}^G$ and $\hat{y}_{C_k}^G$ are sequentially obtained by $$\hat{z}_{C_k}^G = \hat{p}_{AC_k}^G = \frac{p_{AC_k}^G}{\|p_{AC_k}^G\|} \tag{29}$$

$$\hat{x}_{C_k}^G = \hat{p}_{CW_k}^G - (\hat{p}_{CW_k}^G)^T \cdot \hat{p}_{AC_k}^G \cdot \hat{p}_{AC_k}^G \tag{30}$$

$$\hat{y}_{C_k}^G = \hat{z}_{C_k}^G \times \hat{x}_{C_k}^G \tag{31}$$

With ${}^{G}R_{C_k}(p_w^{C_k}, p_r^c)$ being obtained, magnetic forces of every coil at the global frame can be readily calculated using Equations (7) and (8). After the magnetic field and force vectors of every coil are transformed to the global coordinate frame, the optimal coil currents to generate the desired field and force can be calculated by Equations (6) and (10).

FIGS. 3A-3B show the unit field maps of the mobile parallel electromagnetic coils. In particular, FIG. 3A shows the finite element method (FEM) data of the coils, where the local frame $\{O_c$-$\hat{x}^c\hat{y}^c\hat{z}^c\}$ is defined for the field computation. For different mobile parallel electromagnetic coils, $O^{c_k}$ coincides with $C_k$ in the global coordinate system. FIG. 3B shows the comparison of the calibrated model with the FEM data and experimental data.

The magnetic manipulation system comprises a framework of a field mapping for a general coil and 3D field mapping for the whole system. A neural network is included to calibrate the FEM data in the field map domain of the coil since neural networks have the capability to approximate any nonlinear functions with arbitrary accuracy in finite definition domain. FIG. 3A illustrates the coils of FIG. 1 which has a dimension of rel100 30 mm×125 mm. Its large length-to-diameter ratio (>4), large field map domain and short distance between the coils and field map domain hinder the usage of the dipole model.

For the neural network-based calibration method, COMSOL Multiphysics 5.3 of COMSOL Inc., Burlington, USA is first used to create the FEM of the coils as shown in FIG. 3A. Because the coils are axisymmetric, a 2D simulation is sufficient for establishing the 3D field map. A local reference frame $\{O^c$ -$\hat{x}^c\,\hat{y}^c\,\hat{z}^c\}$ is constructed to compute the magnetic field at any position in the field map domain of a coil. Then, two 9×11 data matrices $-\Phi_{norm}(x^c, z^c)$ and $-\Phi_\beta(x^c, z^c)$ ($x^c \in \{-50, -40, \ldots, 40, 50\}$, $z^c \in \{20, 30, \ldots, 120, 130\}$) are acquired from the FEM data corresponding to the norm and angle of the magnetic field vector, when the coil is excited by currents of about 1 Amp. Definition of the angle $\beta$ is illustrated in FIG. 3A. Third, the real magnetic field vectors at the data points are experimentally measured with a 3D magnetic field sensor (for example, Model: TLE493D W22B6, Infineon Inc.). In order to reduce the error of the FEM-based model, calibration is conducted utilizing the experimental measurement. A three-layer neural network is constructed for the calibration purpose. Its inputs are the coordinates and the corresponding field from simulation, and its output is the calibrated field based on the same coordinates. After training the neural network using the aforementioned simulation and experimental data, additional 8×10 data ($x^c \in \{-45, -35, \ldots, 35, 45\}$, $z^c \in \{25, 35, \ldots, 115, 125\}$) are used to evaluate this method. Results plotted in FIG. 3B show that the calibration method reduces the mean error and standard deviation. After obtaining the 3D field map, the gradient matrix can be calculated by taking derivatives of the field map by Equation (3).

Figure 4:
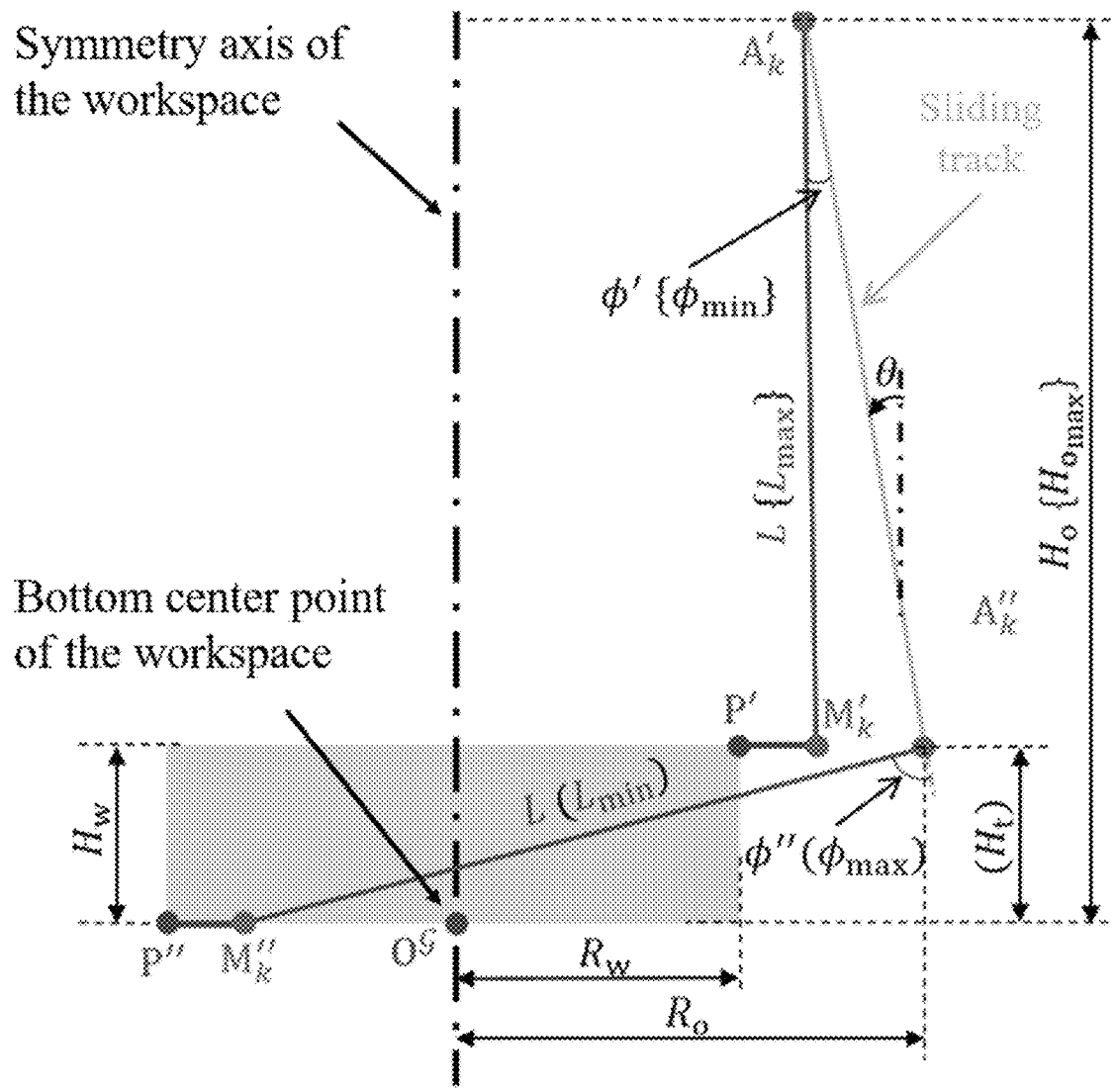
FIG. 4 is a schematic representation illustrating the plane expanded by a symmetry axis of the workspace and the $k^{th}$ sliding track, according to an embodiment of the subject invention.

FIG. 4 shows the representation of the plane expanded by the symmetry axis of the workspace and the $k^{th}$ sliding track. Sliding track as shown in FIG. 1 is one of the actuators that drive the parallel mechanism. Other devices, for example, a ball screw table, rotational joints, can also be used as long as they can fulfill the requirement of the mechanical structure. The superscripts "'" and "''" represents two extreme positions where $\phi$ has its smallest and largest values, respectively. $\{L_{max}\}$ and $\{L_{min}\}$ represent two special cases that L has its maximum and minimum allowed values, respectively. The design of the magnetic manipulation system begins with the workspace which is highlighted in purple in FIG. 4. Considering the axis symmetry of the system, the desired workspace is taken as a cylinder with a radius of $R_W$ and a height of $H_W$. Indicated by Equation (12), the system kinematics can be classified to two categories. As shown in FIG. 4, a bottom center $O^g$ of the workspace is located on the symmetry axis of the work space. In FIG. 4, the methodology of branch design is deduced for $0° \leq \theta \leq 45°$, which can be easily extended to the other category.

The objective of the mechanical design is to ensure that there are no singularities for the kinematics of the parallel mechanism and the field generation, at the same time, the overall system can be as compact as possible. $\phi$ is defined as the intersection angle between the coil branch and its sliding track as shown in FIG. 4. Due to the linear actuation mechanism used in this embodiment, the intersection angle between the coil branch and its sliding track is evaluated to inhibit structural singularities. It can be deduced that $\phi$ has its extreme values, the smallest value $\phi'$ and the largest value $\phi''$ for the whole workspace in this plane. In other embodiments of the invention, however, the relationship between structural linkage and actuation mechanism can be evaluated by other parameters.

In order to inhibit singularities of the parallel mechanism, each coil branch is disposed not to be perpendicular to its sliding track. In addition, the coil branch also cannot be in parallel to its sliding track due to the mechanical constraint. Therefore, the extreme values of $\phi$ satisfy Equation (32):

$$\begin{cases} \phi' \geq \phi_{min} \geq 0° \\ \phi'' \leq \phi_{max} \leq 90° \end{cases} \quad (32)$$

where $\phi_{min}$ and $\phi_{max}$ are flexibly determined constants.

To make a tradeoff between the minimal radius of the overall system $R_o$ and the sufficient space for hardware implementation, $R_o$ is defined by Equation (33):

$$R_o = 1.5R_w + L_{MP} \quad (33)$$

According to FIG. 4, the horizontal coordinate of the bottom end of the sliding track equals $R_o$. To suppress the overall height of the overall system Ho, vertical coordinate of the bottom end of each sliding track $H_t$ is to be minimized. This value is obtained when $\phi''$ reaches $\phi_{max}$, based on Equation (34):

$$H_t = \frac{R_o + R_w - L_{MP}}{\tan(\Phi_{max} - \theta)} \quad (34)$$

After positions of the sliding tracks being obtained, the length of the coil branch L is the only undetermined structural parameter. Optimization is utilized to solve the length of L. First, the optimization domain $(L_{min}, L_{max})$ is deduced. As shown in FIG. 4, if $\Phi''$ equals $\Phi_{max}$, the coil branch length has its allowed minimum value $L_{min}$ which can be calculated by Equation (35):

$$L_{min} = \frac{R_o + R_w - L_{MP}}{\sin(\Phi_{max} - \theta)} \quad (35)$$

Similarly, L has its allowed maximum value $L_{max}$ when $\Phi''$ equals $\Phi_{max}$. By Sine theorem, $L_{max}$ is calculated by Equation (36)

$$L_{max} = \frac{(R_o - R_w - L_{MP} - \Delta H \tan\theta)\sin(90° - \theta)}{\sin\Phi_{min}} \quad (36)$$

-continued where $$\Delta H = H_w - \frac{R_o + R_w - L_{MP}}{\tan(\Phi_{max} - \theta)} \quad (37)$$

The maximum available $H_w$ can be obtained by system constrains: (1) $L_{max} > L_{min}$ (2) $A_k'$ does not coincide with the symmetry axis of the system, i.e. $L_{max} \sin(\theta - \Phi_{min}) < R_w + L_{MP}$. Let $H_{w1}$ and $H_{w2}$ be the solutions of $L_{max} = L_{min}$ and $L_{max} \sin(\theta - \Phi_{min}) < R_w + L_{MP}$, respectively, then $H_w$ satisfies formula (38):

$$H_w < \min(H_{w1}, H_{w2}) \quad (38)$$

$H_{w1}$ is omitted if $\theta = 0$, under which condition $L_{max}$ is larger than $L_{min}$ for any $H_w$. $H_{w2}$ is omitted if $\theta \leq \phi_{min}$ since, in this case, $A_k'$ will not coincide with the symmetry axis of the system. Apparently, a larger Hw leads to a smaller range $[L_{min}, L_{max}]$.

Performance metrics are required to derive the optimal L. Both motion actuation capability and the field generation capability are taken into consideration in order to optimize the length L. For the motion actuation performance, by the above parameter design, the parallel mechanism is guaranteed to have no singularity, but its kinematics property is considered to optimally choose L. To this end, for a specific L, the Jacobian matrix of the parallel mechanism $J_m$ is derived as follows. Substitute Equations (8) and (10) into Equation (11), then Equation (39) is obtained:

$$(x_p - x_k)^2 + (y_p - y_k)^2 + (z_p - z_k)^2 = L \quad (39)$$

where $$\begin{cases} x_k = (L_h + q_k \sin\theta)\cos\alpha_k - L_{MP}\cos\alpha_k \\ y_k = (L_h + q_k \sin\theta)\sin\alpha_k - L_{MP}\sin\alpha_k \\ z_k = L_V - q_k \cos\theta \end{cases} \quad (40)$$

$L_h$ and $L_V$ are expressed by $$\begin{cases} L_h = R_w + L_{MP} - L\sin(\theta - \phi') \\ L_V = H_o = H_W + L\cos(\theta - \phi') \end{cases} \quad (41)$$

Where $\phi'$ is calculated by Equation (42):

$$\phi' = \arcsin\left(\frac{(R_o - R_w - L_{MP} - \Delta H \tan\theta)\sin(90° - \theta)}{L}\right) \quad (42)$$

Differentiating Equation (39) with respect to time leads to Equation (43):

$$(x_p - x_k)\dot{x}_p + (y_p - y_k)\dot{y}_p + (z_p - z_k)\dot{z}_p = D_k \dot{q}_k \quad (43)$$

Where $$D_k = (x_p - x_k) \sin\theta \cos\alpha_k + (y_p - y_k) \sin\theta \sin\alpha_k - (z_p - z_k)\cos\theta \quad (44)$$

Equation (39) is rearranged to obtain Equation (45):

$$\dot{q} = J_m \dot{p}_P^G \quad (45)$$

The Jacobian matrix is shown by Equation (46):

$$J_m = \begin{bmatrix} \frac{x_P - x_1}{D_1} & \frac{y_P - y_1}{D_1} & \frac{z_P - z_1}{D_1} \\ \frac{x_P - x_2}{D_2} & \frac{y_P - y_2}{D_2} & \frac{z_P - z_2}{D_2} \\ \vdots & \vdots & \vdots \\ \frac{x_P - x_k}{D_k} & \frac{y_P - y_k}{D_k} & \frac{z_P - z_k}{D_k} \end{bmatrix} \quad (46)$$

The reciprocal of the condition number of $J_m$ is selected as the performance metrics for the motion actuation as shown in Equation (47):

$$\mu_m = \frac{1}{\kappa_m} \quad (47)$$

where $\kappa_m = \|J_m^\dagger\| \cdot \|J_m\|$ and $\|\cdot\|$ denotes the second norm of the matrix. $\mu_m$ has a value range of $[0,1]$ that reflects the distance to the actuation singularity. $\mu_m = 0$ indicates that the parallel mechanism enters its singularity so that it is out of control. On the contrary, the larger the $\mu_m$ is, the farther the distance to singularities is and the more isotropic actuation capability is. Although $\mu_m$ is only a local index, its average—AVG ($\mu_m$) and minimum MIN ($\mu_m$) can be used over the whole workspace to evaluate the overall system performance.

In a similar manner, the field generation performance can be evaluated. Different from the mechanical mechanism, coil currents can be controlled to be at an arbitrarily high speed. Therefore, instead of considering the kinematics, the properties of $\hat{H}^\dagger$ in Equation (6) can be directly used for the performance evaluation of AVG ($\mu_h$) and minimum MIN ($\mu_h$), in which $$\mu_h = \frac{1}{\kappa_h} \text{ and } \kappa_h = \|\hat{H}^\dagger\| \cdot \|\hat{H}\|. \quad (48)$$

The method to quantify the overall system performance is to construct a composite performance metrics Q as shown by Equation (49)

$$Q = W_1 \cdot AVG(\mu_m) + W_2 \cdot MIN(\mu_m) + W_3 \cdot AVG(\mu_h) + W_4 \cdot MIN(\mu_h) \quad (49)$$

where $W_1$ to $W_4$ are constant weights.

This optimal coil branch length $L_{opt}$ that results in the largest Q can be found by offline simulations, after which the corresponding $\phi_{opt}'$ and $\phi_{opt}''$ are obtained by substituting $L_{opt}$ into Equation (42) and Equation (50), respectively.

$$\phi_{opt}'' = \arcsin\left(\frac{L_{min}\sin(180° - \phi')}{L_{opt}}\right) \quad (50)$$

The necessary length of the sliding track $L_{st}$ is readily computed by Equation (51):

$$L_{st} = \frac{(R_o - R_w - L_{MP} - \Delta H \tan\theta)\sin(90° + \theta - \phi_{opt}')}{\sin(\phi_{opt}')} + \frac{\Delta H}{\cos\theta} - \frac{L_{min}\sin(\phi_{max} - \phi_{opt}'')}{\sin\phi_{opt}''} \quad (51)$$

With the established methodology, embodiments of the invention can be designed and constructed to show the manipulation of magnetic devices using multiple mobile coils.

Figure 5:
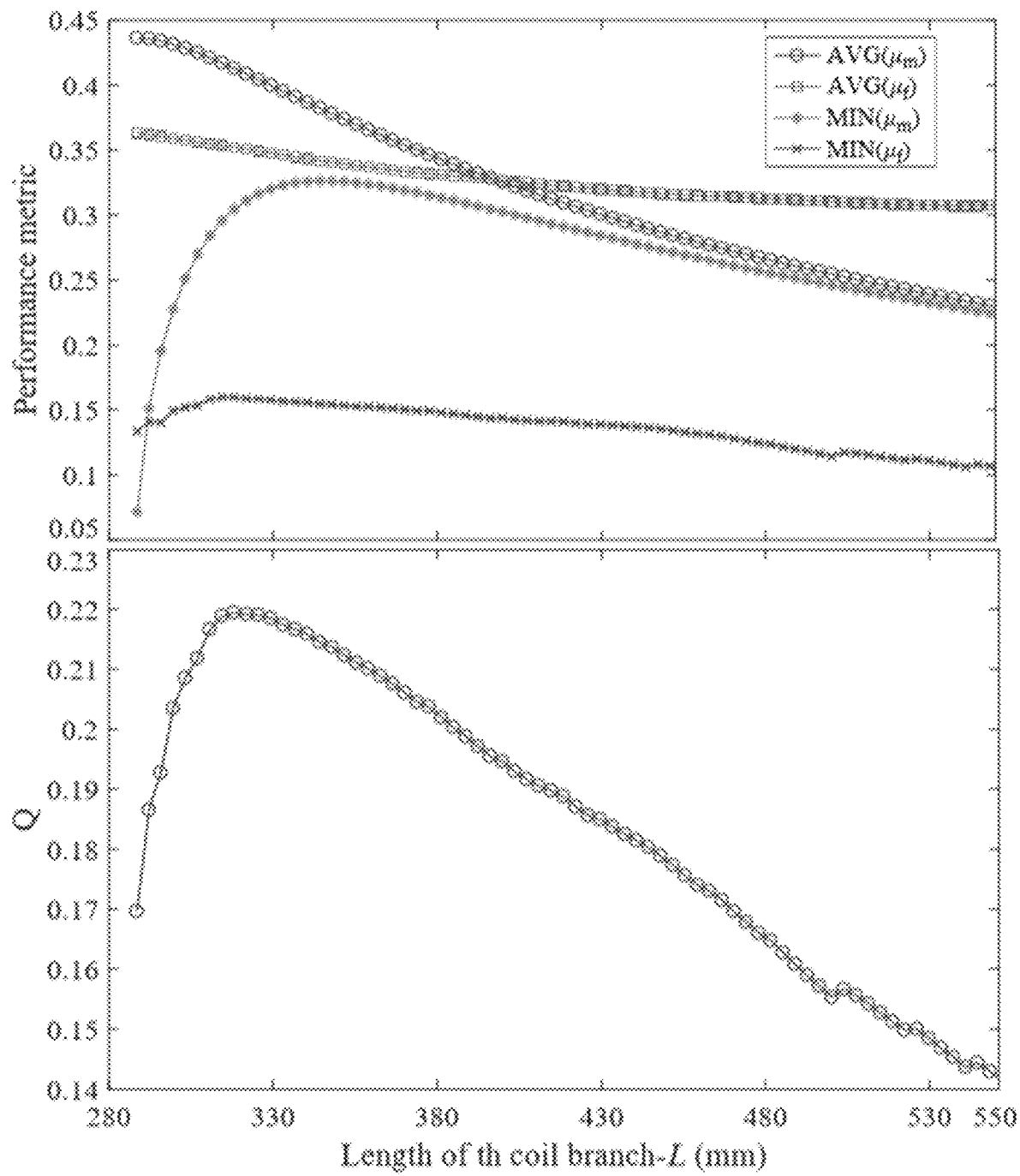
FIG. 5 shows plot diagrams of performance simulation results with K=3 and θ=0° for different coil branch lengths, according to an embodiment of the subject invention.
Figure 7:
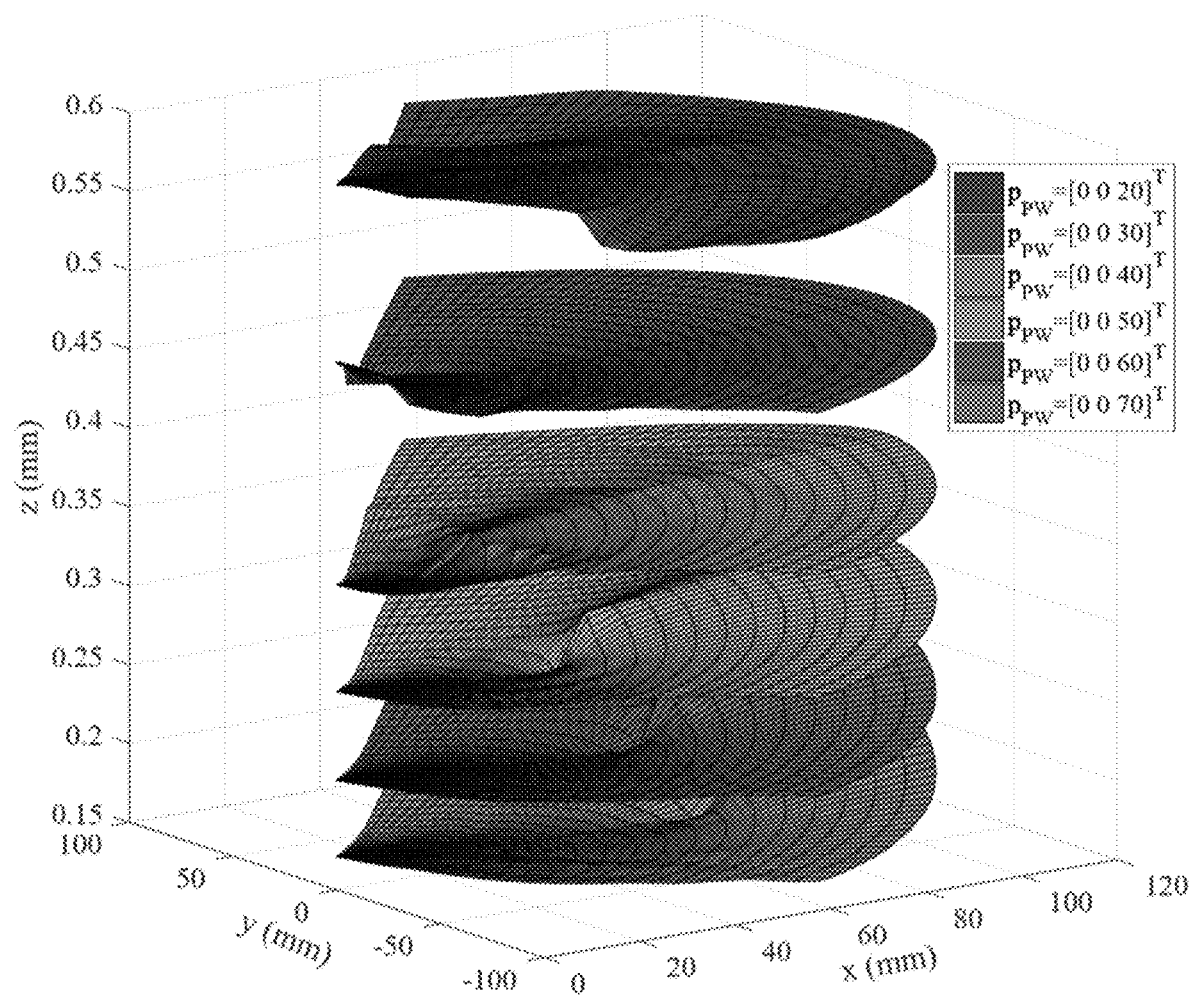
FIG. 7 shows results of field generation performance for the optimized coil branch length $L_{opt}$ when the relative position between the coil-end plate and the magnetic device varies, according to an embodiment of the subject invention.

FIG. 5 depicts the performance simulations for an embodiment of the invention having different coil branch lengths. For each L from $L_{min}$ to $L_{max}$, $\mu_m$ and $\mu_h$ are computed with 12010 sample points for AVG ($\mu_m$), AVG ($\mu_h$), MIN ($\mu_m$) and MIN ($\mu_h$). In addition, five $p_{PW}$ shown in FIG. 7 are also computed for AVG ($\mu_h$) and MIN ($\mu_h$). The composite performance metric Q used to determine the optimal L is computed by Equation (49).

Based on the optimization results, the optimal link length $L_{opt}$ can be obtained. With the required workspace radius ($H_{w1}$ and $H_{w2}$) being confirmed, the total height $H_w$ can be determined. In order to accommodate the magnetic coils in the structure of the parallel mechanism, the coil length has to be smaller than the diameter of the workspace. The coils used here have predetermined diameters and lengths and are equipped with soft iron cores. The coils have large length-to-diameter ratio and their magnetic fields can be accurately modelled by the method mentioned above. Then the relevant key parameters can be directly computed by the method discussed above.

Figure 6A:
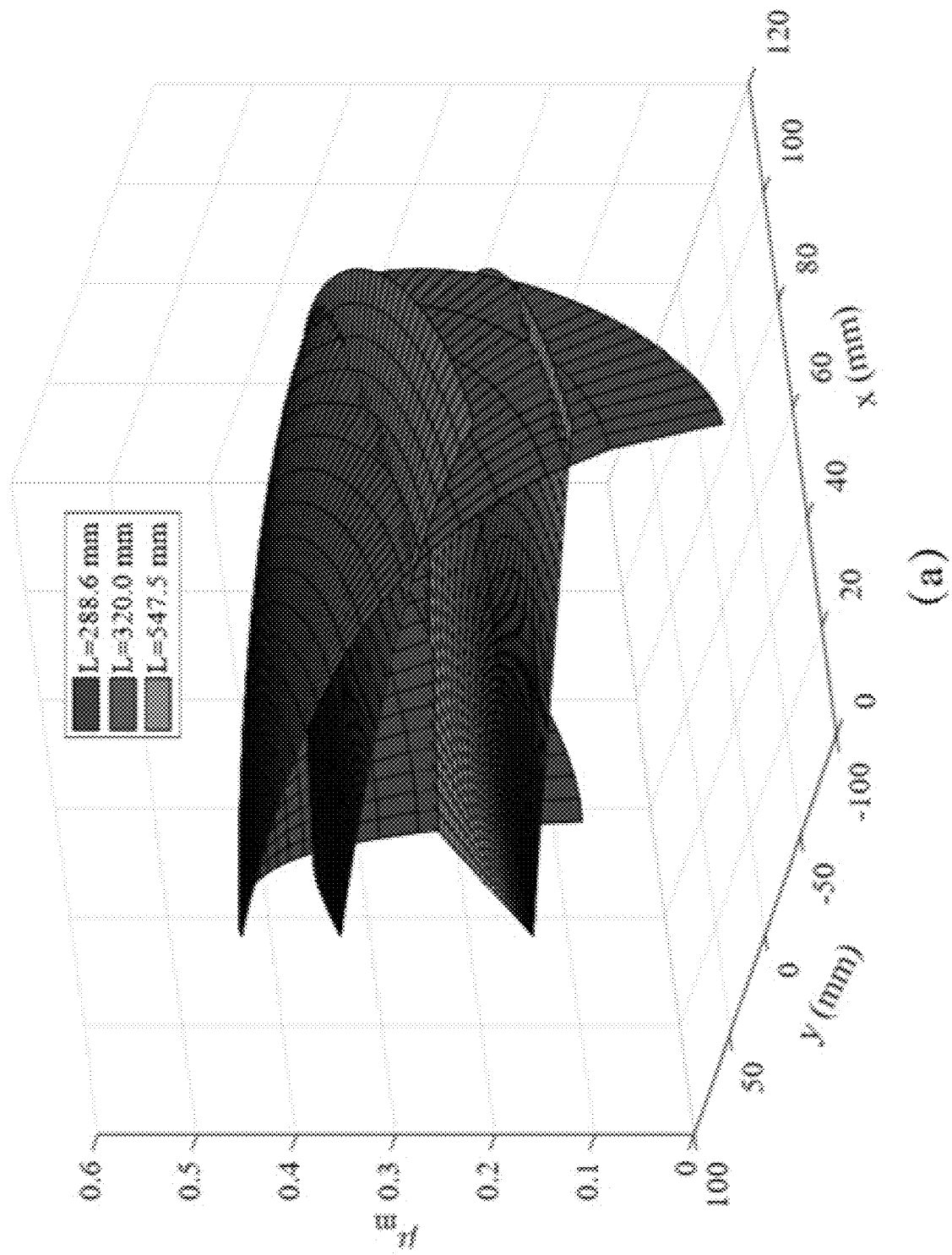
FIGS. 6A-6B are plot diagrams of performance metrics of the whole workspace, according to an embodiment of the subject invention.
Figure 6B:
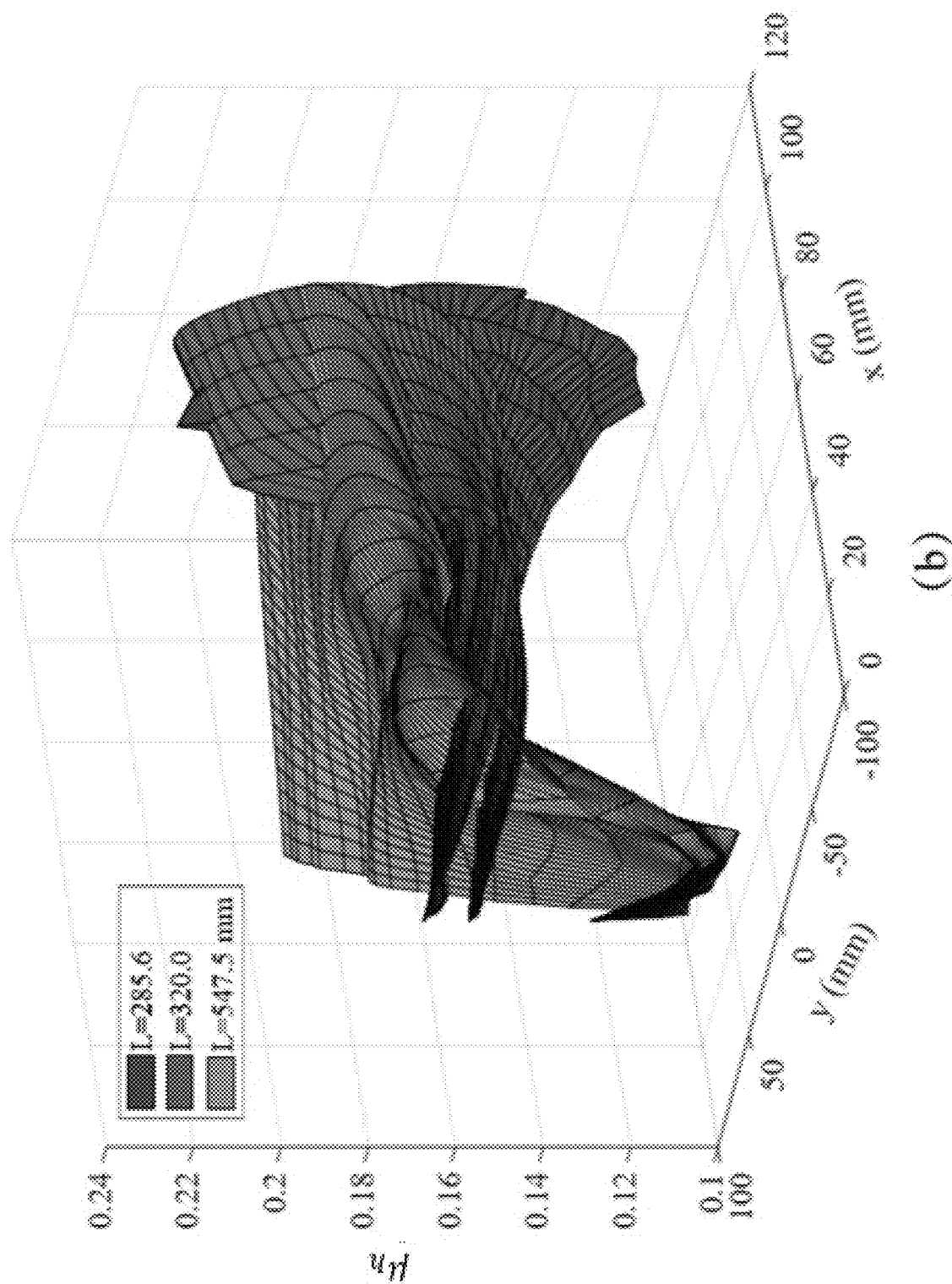

FIGS. 6A-6B show the performance metrics in the whole workspace. Due to the system symmetry, simulations are conducted for one third of the cylindrical workspace. $\mu_m$ is the evaluation parameter of the motion metrics and $\mu_h$ is the evaluation parameter of the magnetic field generation. In particular, FIG. 6A shows the distributions of the kinematics metric for three coil branch lengths which are near $L_{min}$, $L_{opt}$ and $L_{max}$, respectively. FIG. 6B shows the distributions of the field generation metric for the three coil branch lengths. The shorter the L is, the more nonuniform the $\mu_m$ distribution becomes. According to FIG. 6B, the distribution of $\mu_h$ becomes irregular due to the nonlinearities of the kinematics of the parallel mechanism and the field distribution of the coils. At some locations, $\mu_h$ has very small values near 0.1 when L is close to $L_{min}$ or $L_{max}$. This issue can be inhibited by optimizations.

FIG. 7 illustrates the visualization of $\mu_h$ in the workspace for six different $p_{PW}$. Results demonstrate that although there are no singularities, the field generation performance decreases for each working position when $p_{PW}$ is increased, indicating that compared to conventional stationary coil systems, the magnetic manipulation and navigation system of the embodiments of the subject invention keep as close as possible to the manipulated devices, by which the field generation performance is maximized.

Figure 8A:
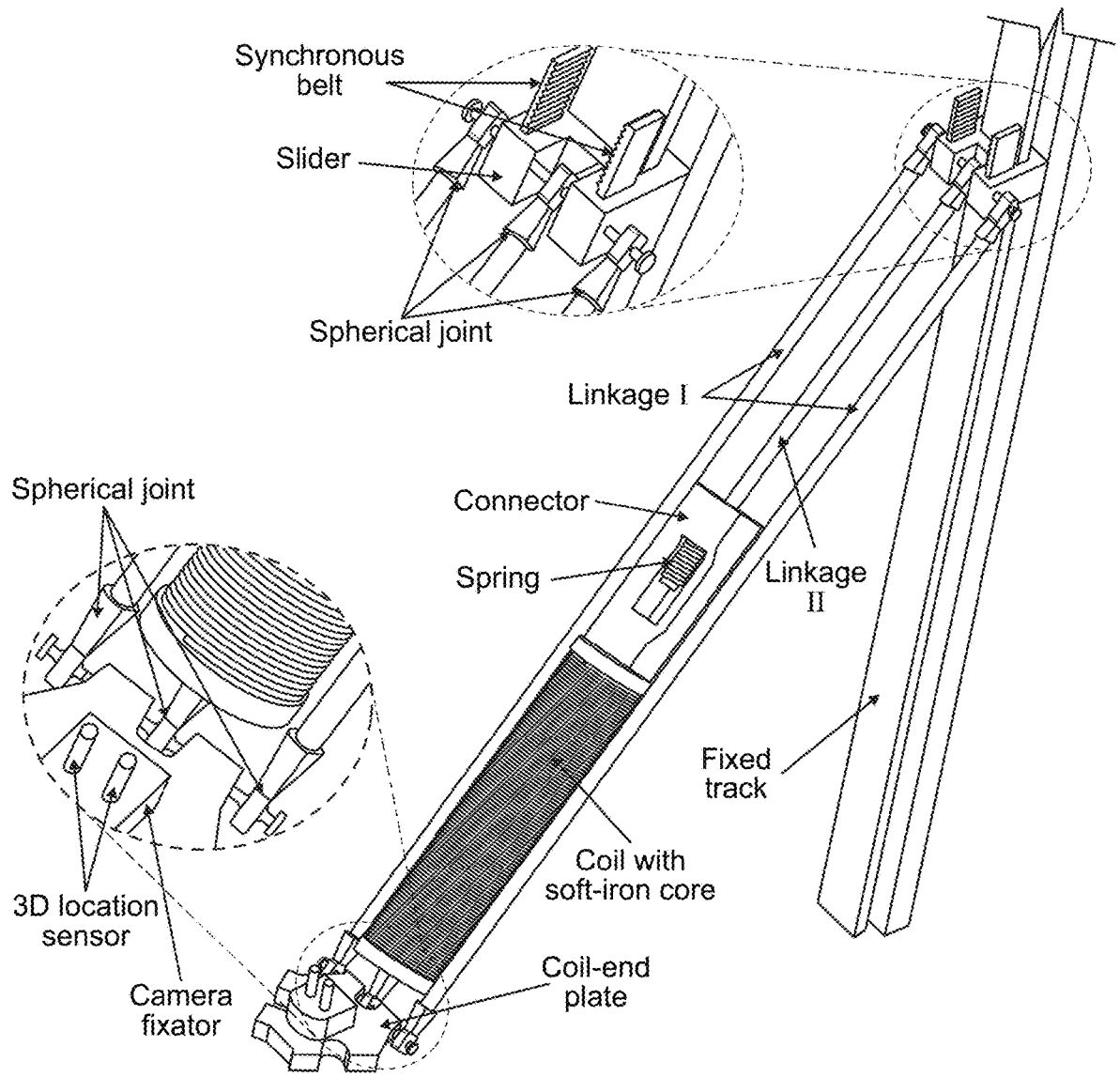
FIGS. 8A-8C are schematic representations illustrating the mechanical design of the magnetic manipulation system, which includes the coil-branch and the coil-end plate, according to an embodiment of the subject invention.

FIG. 8A illustrates the mechanical design of the embodiment of the invention including the coil branch and the coil-end plate. Structural materials utilized by the system have negligible magnetic permittivity. To constrain the pose of the coil-end plate to be invariant, each coil branch has a parallelogram mechanism realized by the slider, the coil-end plate and two linkages (Linkage I) with four spherical joints for linking them as shown in FIG. 8A. The coil is integrated into the parallelogram mechanism via two spherical joints, a linkage (Linkage II) and a connector. By this embodiment, the coil branch contains two identical parallelogram mechanisms that ensure the required 3D motion of the coil-end plate. A spring is utilized between the connector and Linkage II so that this mechanism is robust to the fabrication error. Synchronous belts are used to actuate the sliders in the embodiment. For other embodiments, alternative rigid actuators (for example, a ball-screw mechanism or the linear motors) can be employed.

Figure 8B:
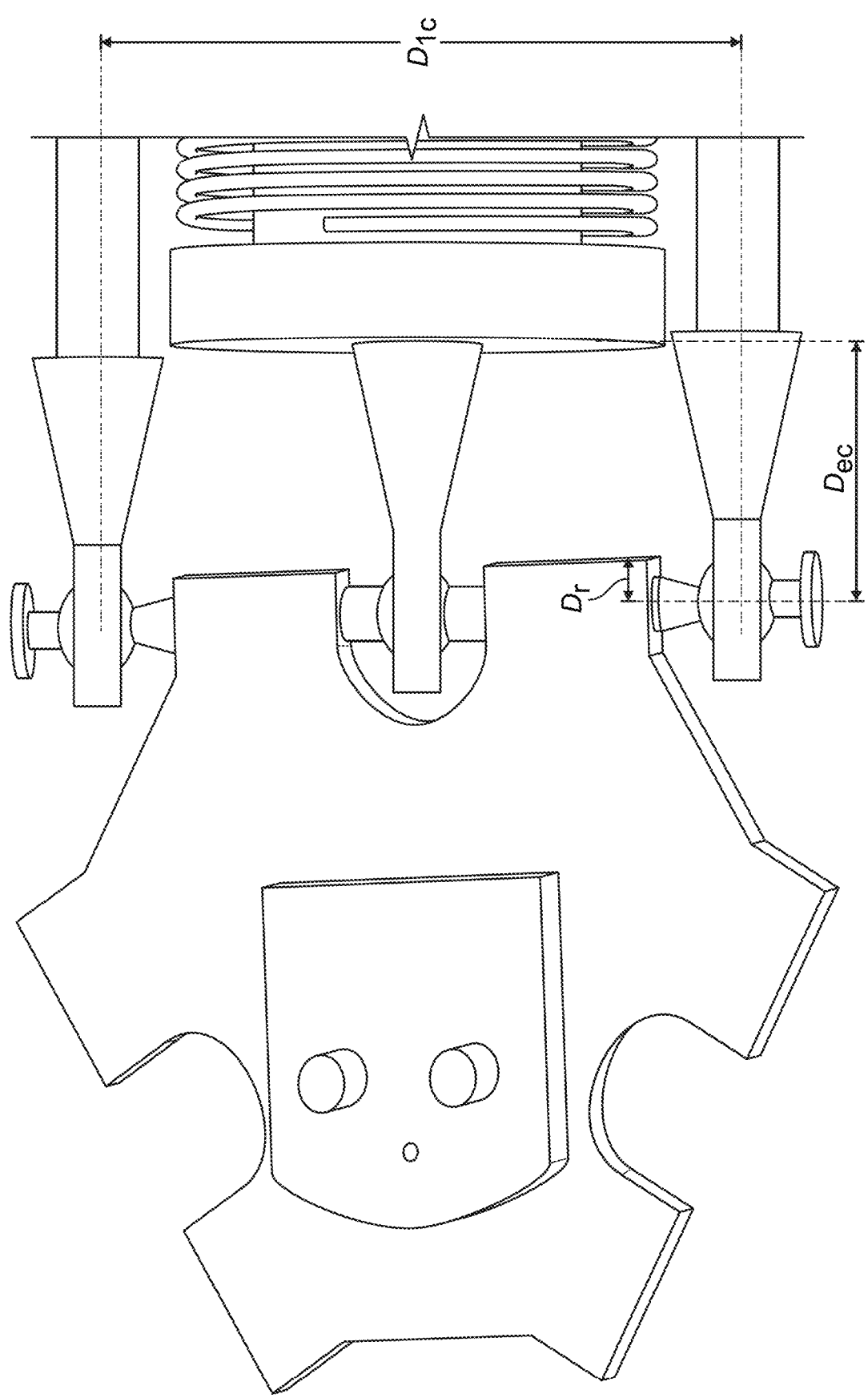

FIG. 8B shows the design of coil-end plate. The distance between the two spherical joints of the two Linkages I ($D_{lc}$) are carefully selected to inhibit collision between the coil and the two Linkages I. As a result, the minimum distance between the two Linkages I is required to be larger than the coil diameter. Derived from the geometric relationship, this requirement is equivalent to formula (52):

$$D_{lc} > \frac{2R_c L_{opt}}{\sqrt{L_{opt}^2 - R_w^2}} + 2R_1 \tag{52}$$

where $R_c$ and $R_1$ are the radius of the coil and Linkage I, respectively. On the other hand, the distance between the coil-end plane and the coil-end plate ensure that the two do not collide, when formula (53) is satisfied:

$$D_{ec} > \frac{R_c w}{\sqrt{L_{opt}^2 - R_w^2}} + D_r \tag{53}$$

where $D_r$ stands for the distance from the spherical joint shaft to the surface of the coil-end plate as shown in FIG. 8B. The value of $L_{MP}$ has to be large enough to ensure the coil branches does not collide with each other based on the formula (54):

$$L_{MP} > \frac{D_{lc}/2 + \Delta D}{\tan\left(\frac{360°}{2K}\right)} \tag{54}$$

where $\Delta D$ is the distance required to mount the Linkage I as shown in FIG. 8B.

In order to inhibit the magnetization of the mechanical structures that would influence the magnetic field of the coils, structural materials having negligible magnetic permittivity is used. For example, the coil-end plate is fabricated by aluminum alloy and linkages are made of 304 steel.

Figure 8C:
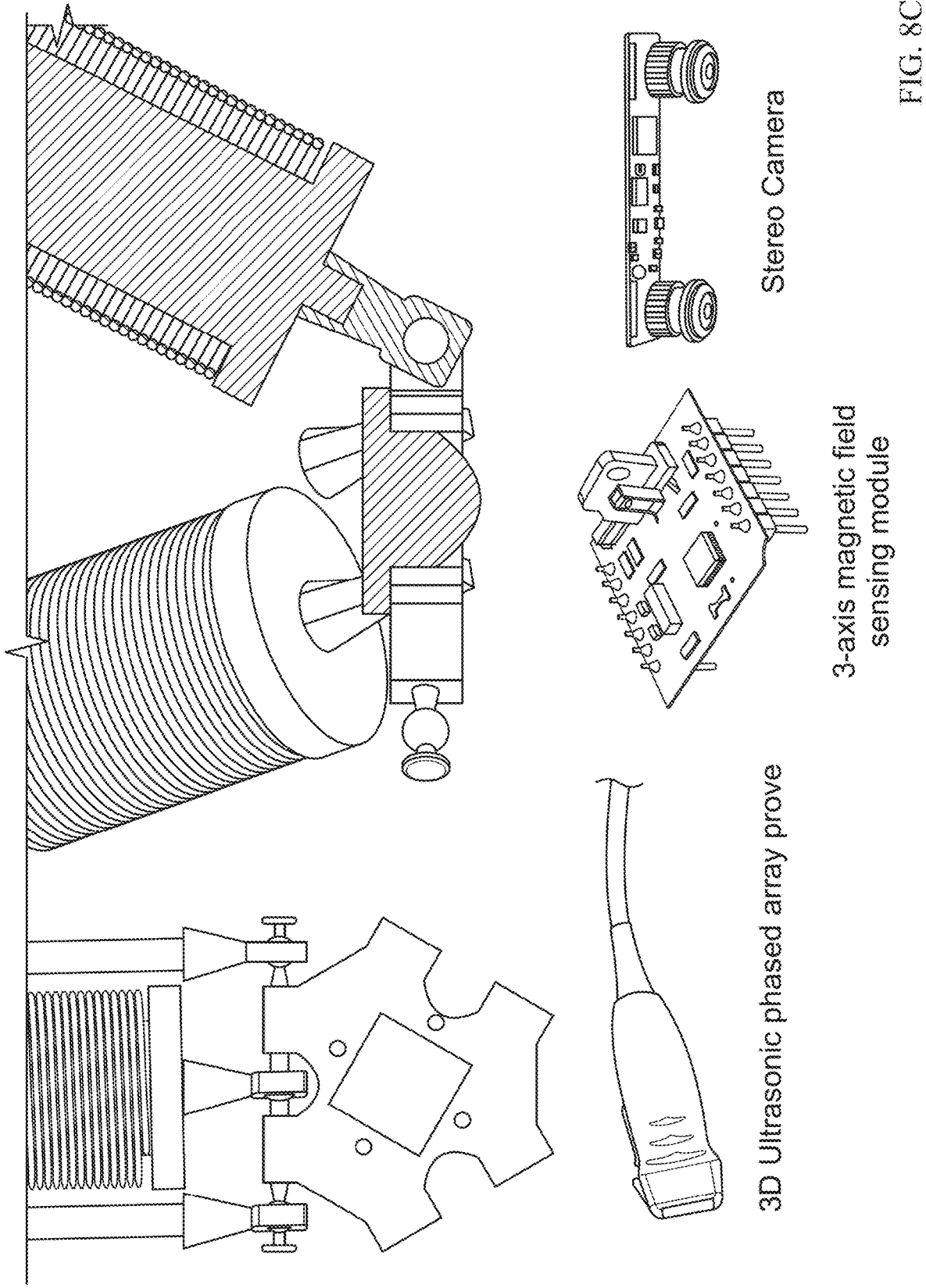

FIG. 8C illustrates the design of the interchangeable instrument module. The coil-end plate is customized for installing various 3D location sensors or medical imaging devices. The embodiment shown in FIG. 8C is squared-hollow in the middle where instrument can be installed. Depending on the 3D location feedback methods applied for the close loop control, instruments such as 3D ultrasonic array probe, 3 axis magnetic location module and stereo camera can be applied. Location methods of the system can be adjusted according to the requirement of the task.

Vision based feedback can be used as a valid location method when the controlled objects are captured by cameras. A stereo camera can send 3D location information to the control system. Because of the eye-in-hand configuration of the system, large area vision-based tracking of the controlled object in transparent body can be achieved.

Ultrasound imaging system can be integrated as a sensing tool to feedback the location of controlled object. Such location method can be used when the controlled objects are in animal or human body. Under such condition, cameras cannot capture the image of the controlled objects and thus vision-based location feedback is not available. A 2D/3D ultrasound sensor can be installed on the coil-end plate. Localizing and tracking of the controlled objects is realized by analyzing the resulting images.

Magnetic localization is a valid localization method for tracking controlled. By implanting magnetic sensors on the coil-end plate, 3D magnetic sensors can detect the magnetic objects in the body. Same as ultrasound imaging system, magnetic localization method can be used in controlling objects in a body where the controlled target cannot be captured by the cameras.

Different localization tools can be encapsulated as a sensing module individually and can be respectively installed under different requirements. The coil-end plate is designed as an instrument platform where various kinds of 3D location sensors can be integrated.

Figure 9:
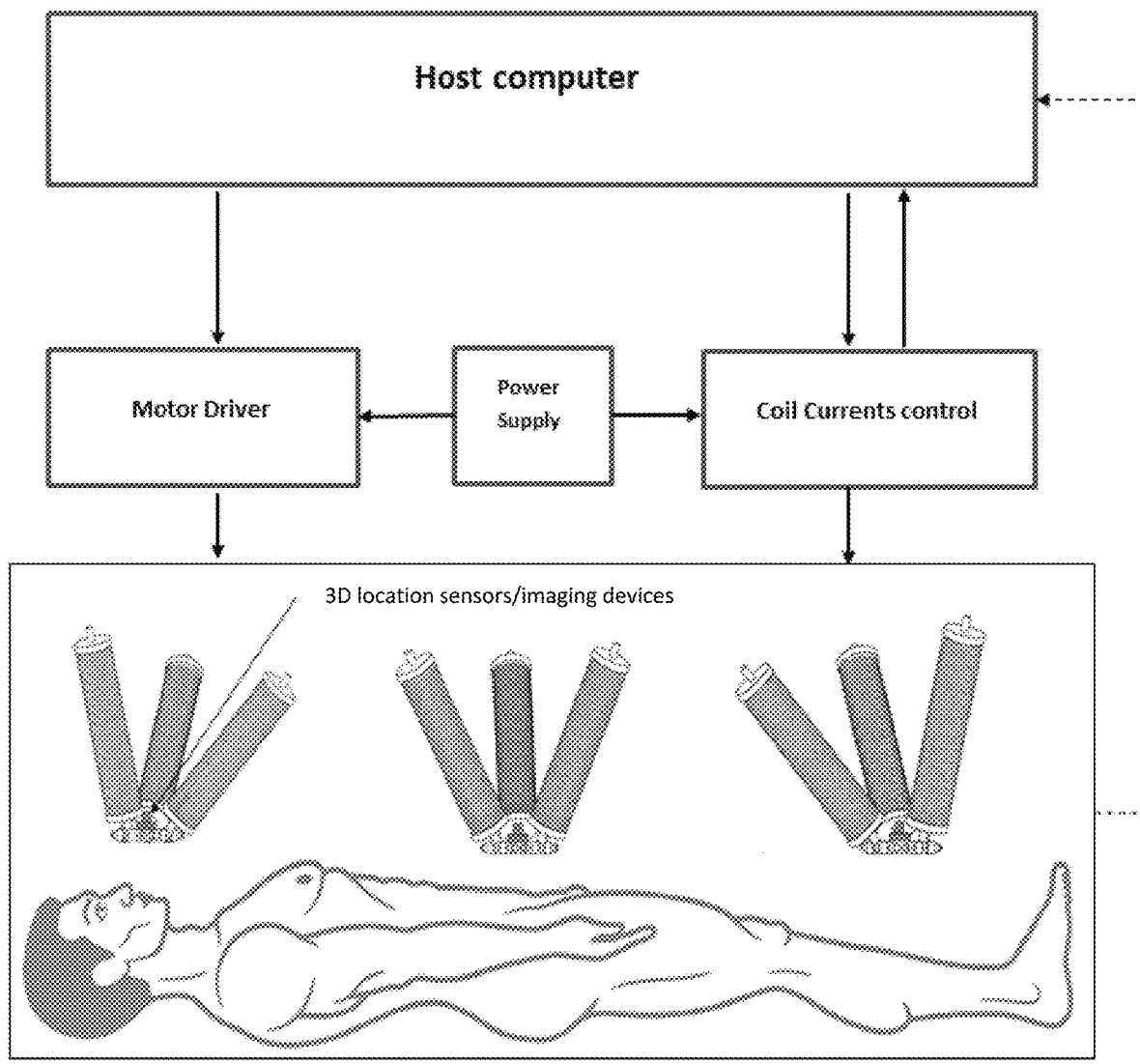
FIG. 9 is a block diagram of the magnetic manipulation system, according to an embodiment of the subject invention.

FIG. 9 is a block diagram of the magnetic manipulation system comprising the mechanical system, the coil actuation and control module, the motor actuation and control module, and the host computer, as well as the signaling relationships among them. In the embodiment, the parallel coil mechanism is driven by stepper motors via synchronous linear actuators. A power supply is adopted for power delivery. Each motor is sufficient for moving the coil branches. When receiving the updated positions of the coil-end plate, a microcontroller computes the inverse kinematics of the parallel mechanism and generates control signals to the motor actuators to control the motion of the motors. A stereo camera comprising two micro-endoscopes is installed on the coil-end plate to track the 3D position of the controlled device for feedback control. Owing to the 'camera-in-hand' configuration, the magnetic manipulation system can integrate with high-resolution and narrow field-of-view sensors for precise control task in a large workspace. Other embodiments can use other 3D position sensors for feedback control. Movement of the coil-end plate is performed by the methods implemented in the host computer in real time based on the feedback position of the controlled device. Serial communication is implemented to send commands to the microcontroller and receive the current position as feedback.

Each of the coils is driven by a servo-amplifier. Their power is delivered by a direct current (DC) power supply assisted by the signal processing and control methods, the computer calculates the desired 3D magnetic field in real time based on the feedback positions of the coil-end plate and the controlled device, and the proposed field generation method is also implemented on the host computer which then generates desired electric currents for the coils. The digital control signal is converted to analog control voltages and sent to the servo amplifiers through a multifunctional I/O card. Dynamic coil currents are generated by the three servo amplifiers in a closed-loop manner to output the desired magnetic field.

Figure 10A:
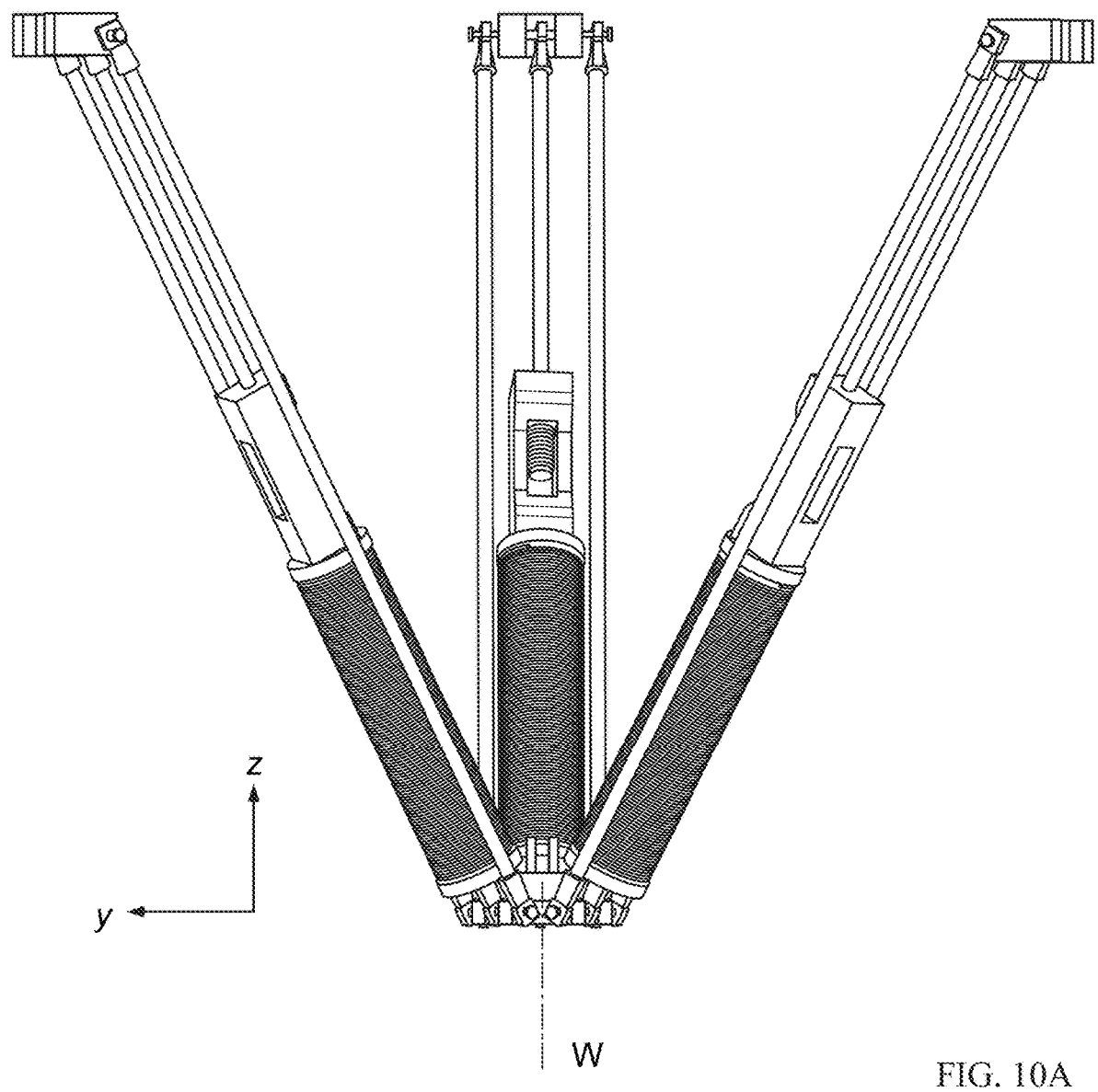
FIGS. 10A-10C are schematic representations illustrating three different mobile parallel coil mechanism, according to an embodiment of the subject invention.
Figure 10B:
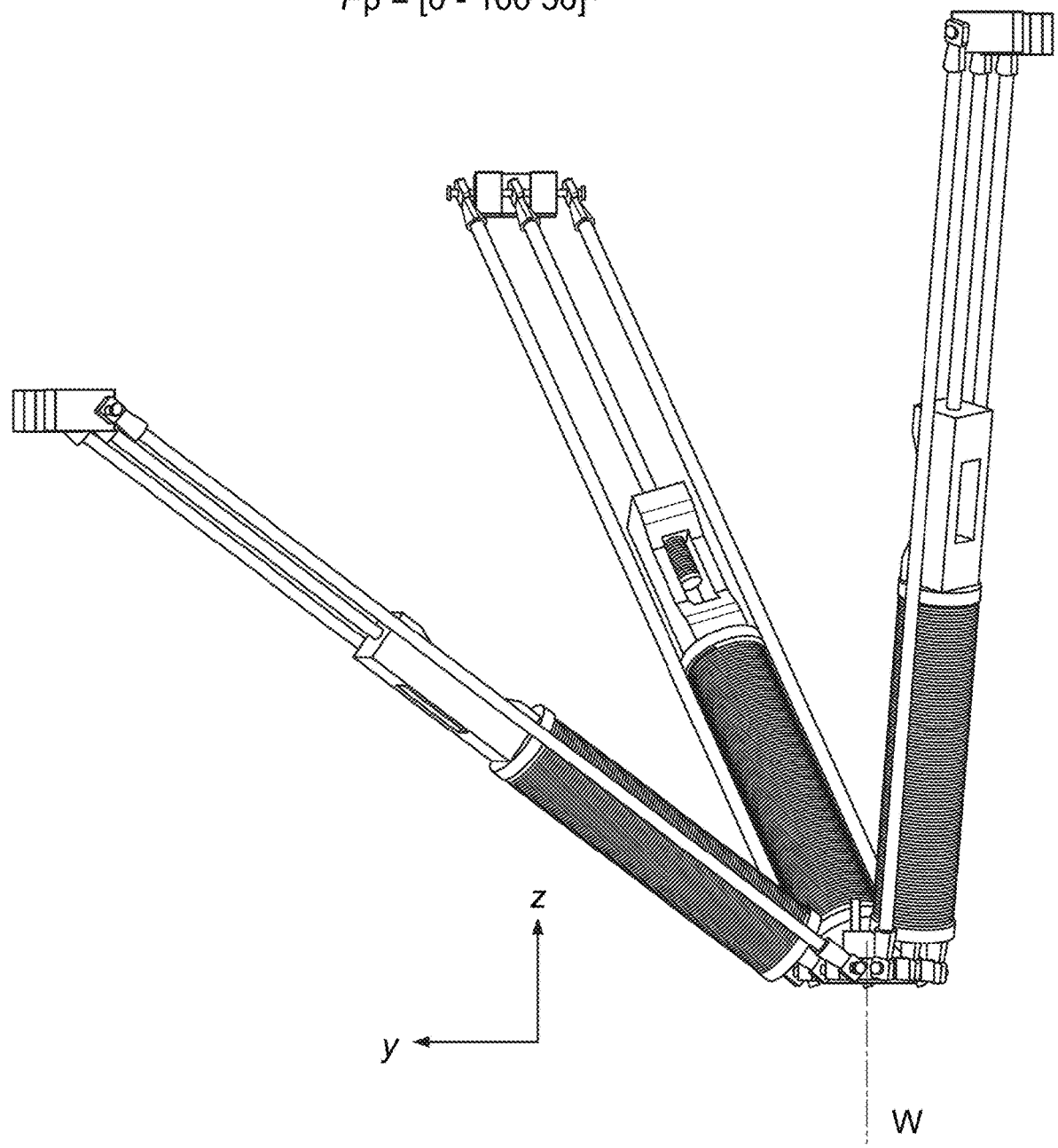
Figure 10C:
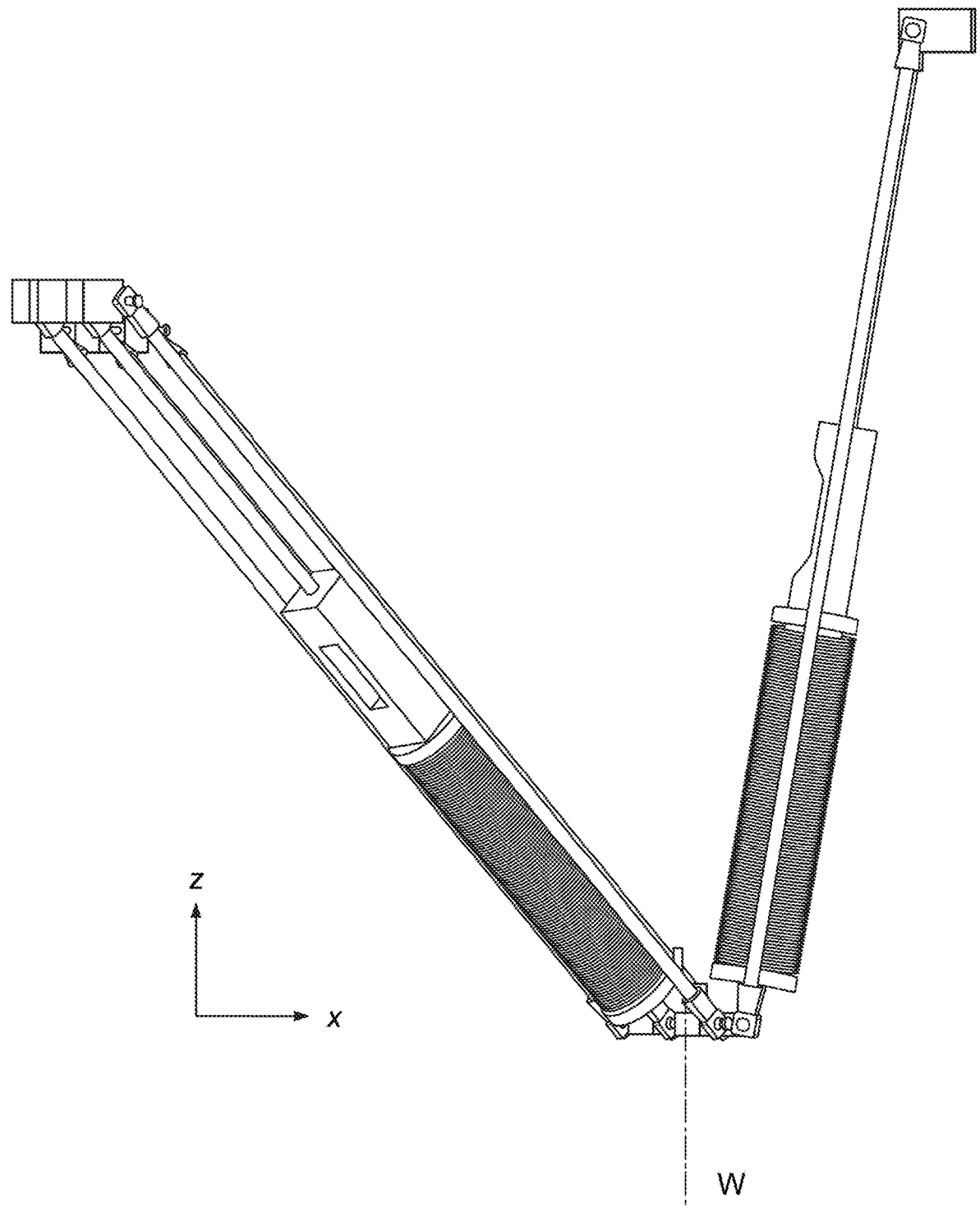
Figure 10D:
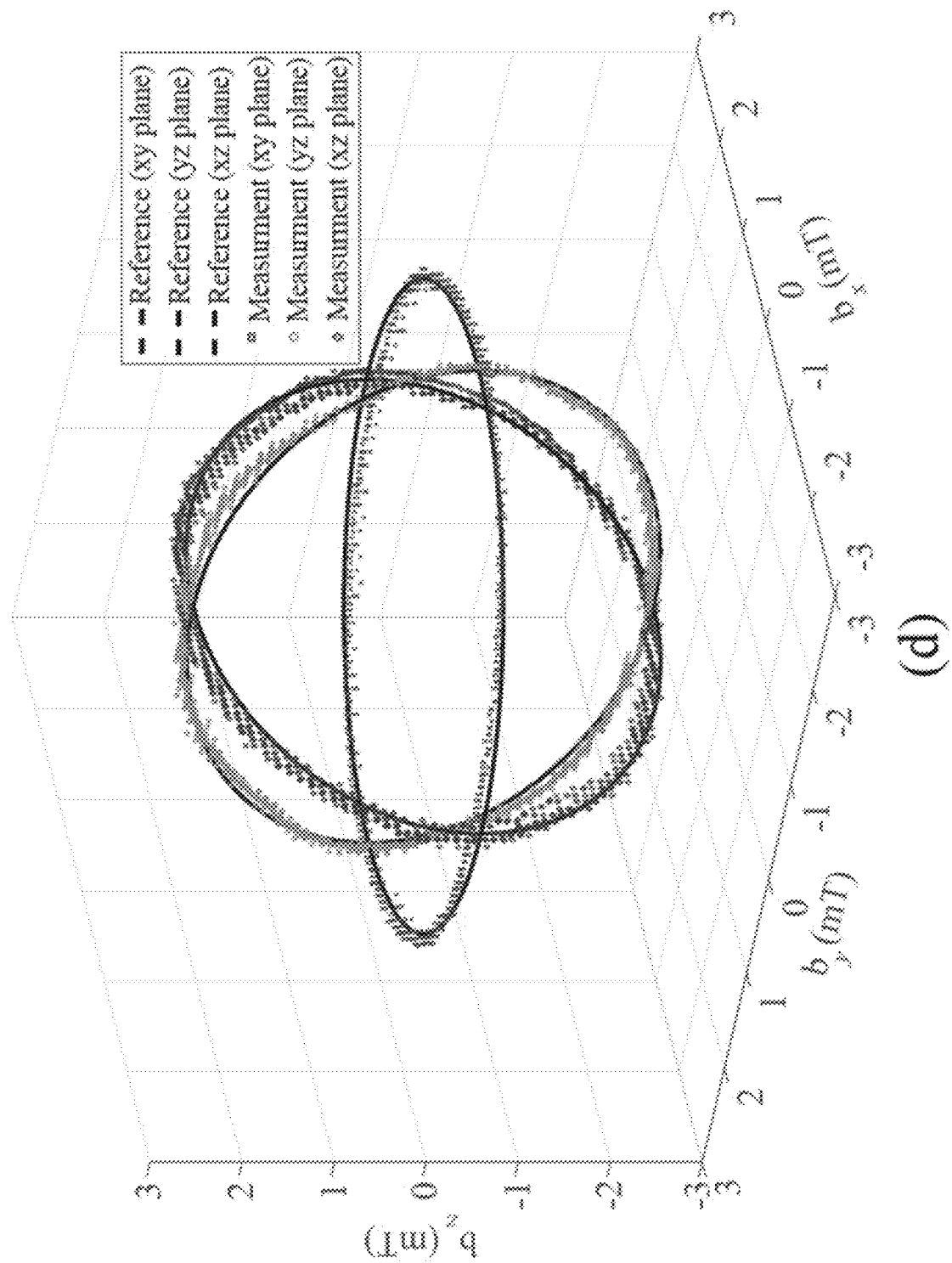
FIGS. 10D-10F shows experimental results of the field generation of the three mobile parallel coil mechanism of FIGS. 10A-10C, respectively, the reference fields for the three mobile parallel coil mechanism being set as circular rotating fields on XY, YZ and XZ planes, respectively, according to an embodiment of the subject invention.
Figure 10E:
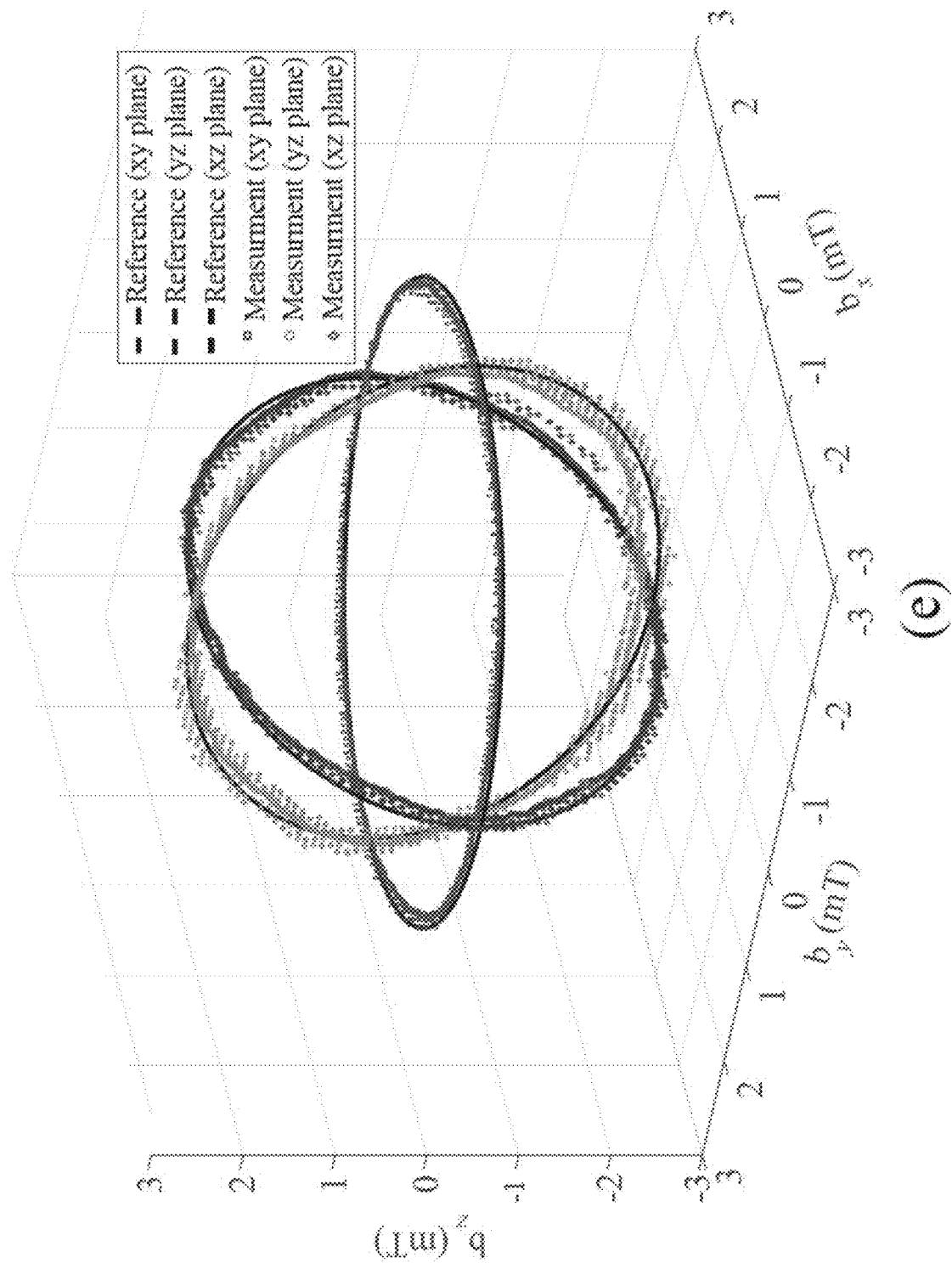
Figure 10F:
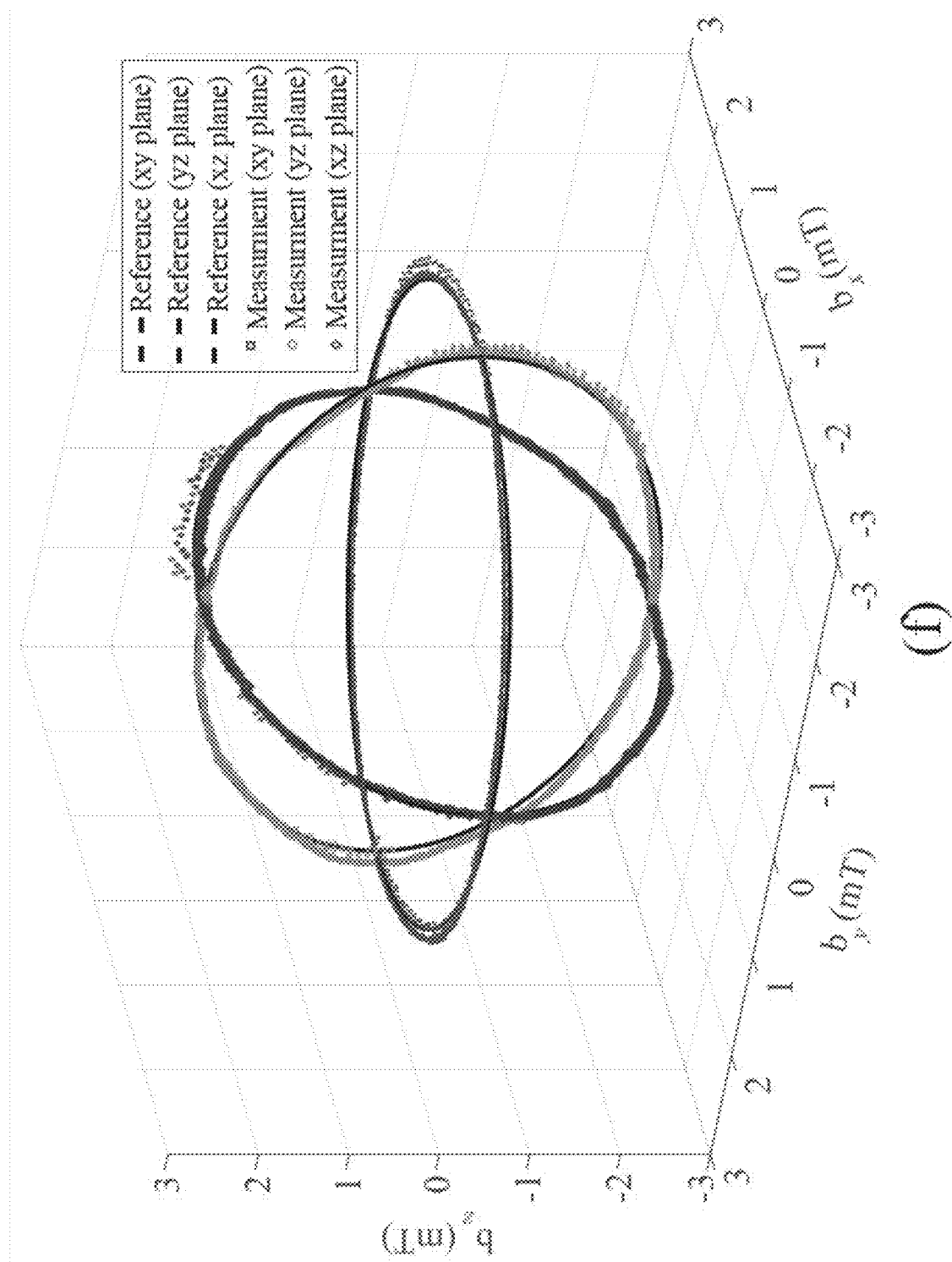

The experimental results of the field generation at three selected mechanism poses are shown in FIGS. 10A-C, respectively. $p_{PW}$ is kept static for all the poses. The reference fields for each pose are set as circular rotating fields at XY, YZ and XZ planes as shown in FIGS. 10D-10F, which can reflect the field generation capability for an arbitrary direction. Overall, the embodiment of the system and field generation methods can generate accurate magnetic fields in a large workspace even with the variation of the coil poses and positions.

Figure 11A:
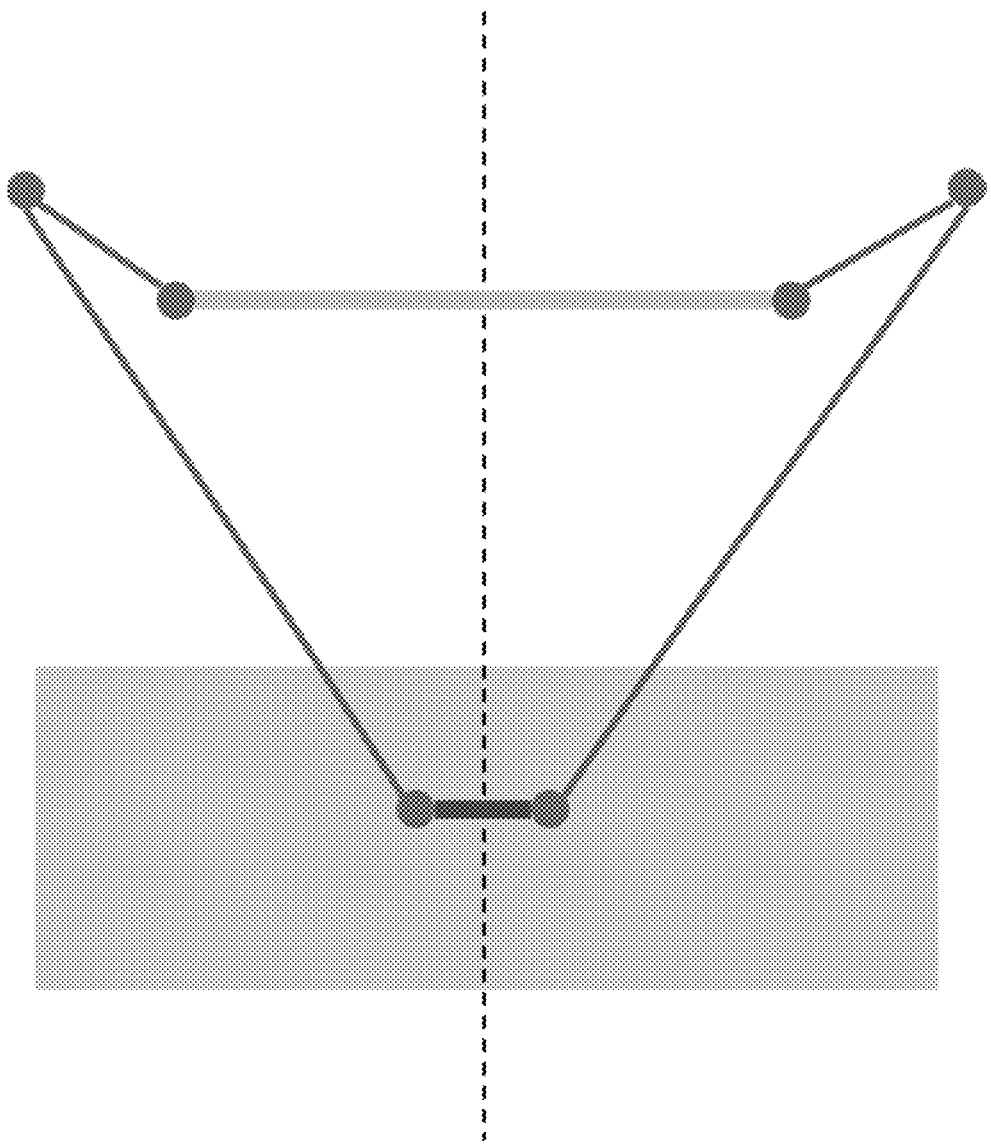
Figure 11B:
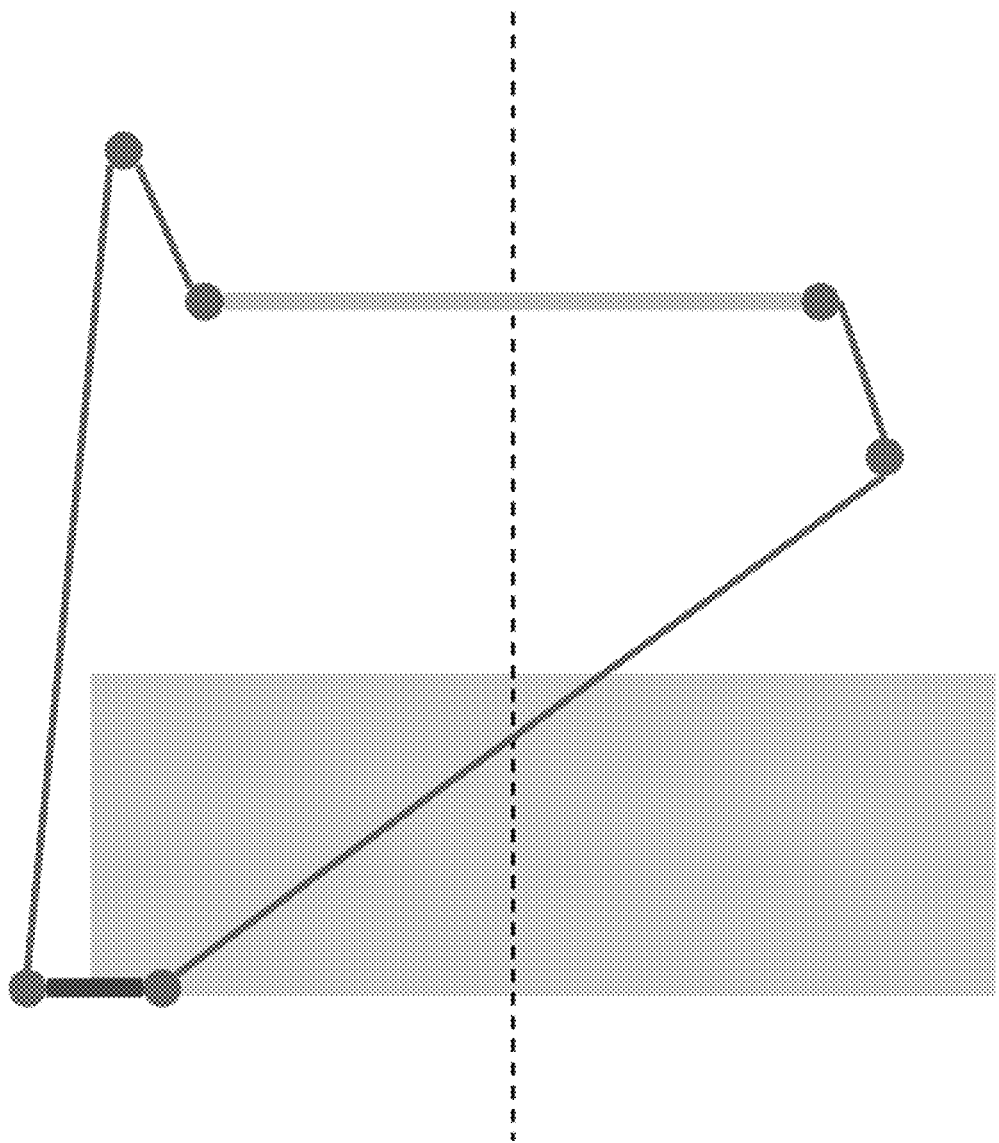
Figure 11C:
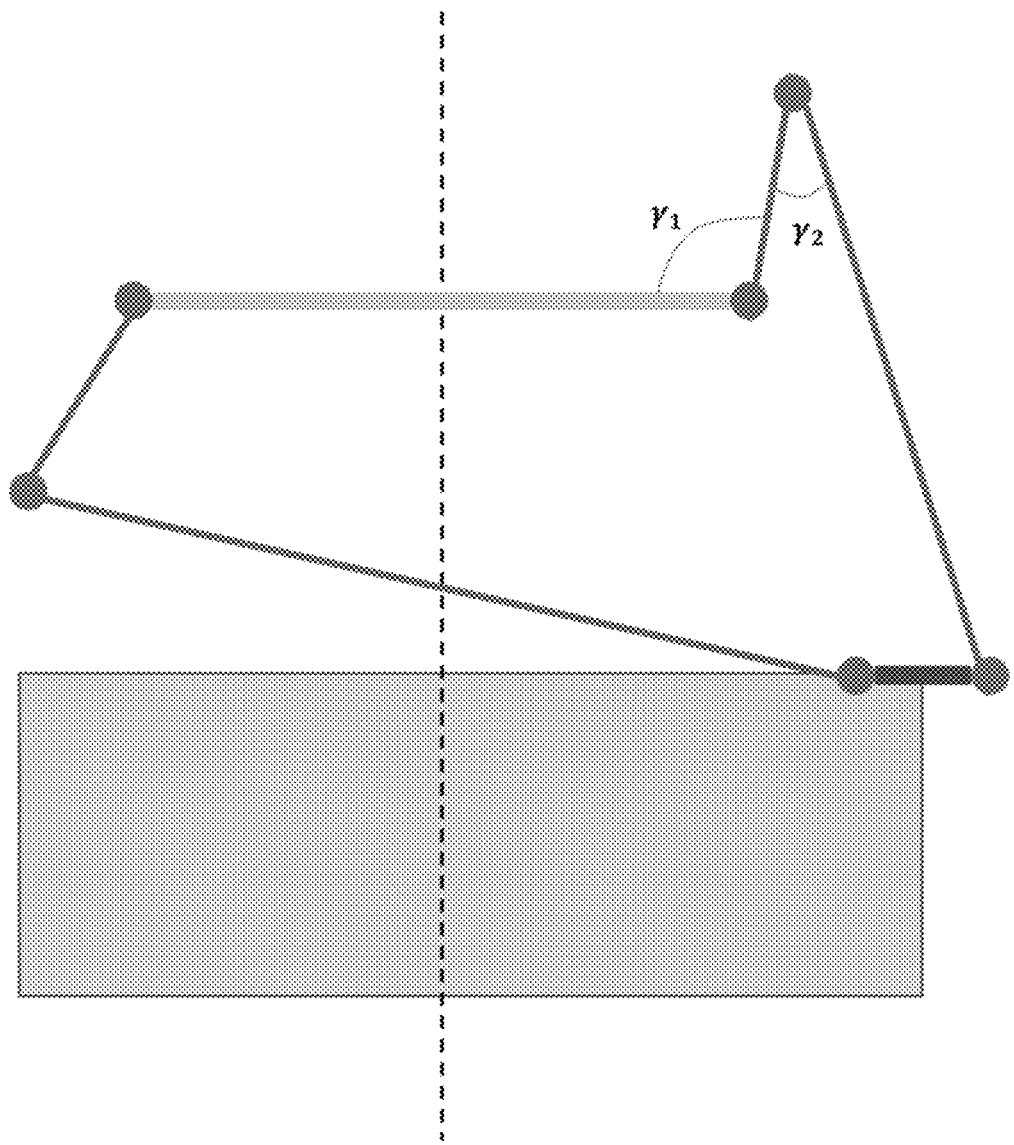
Figure 11D:
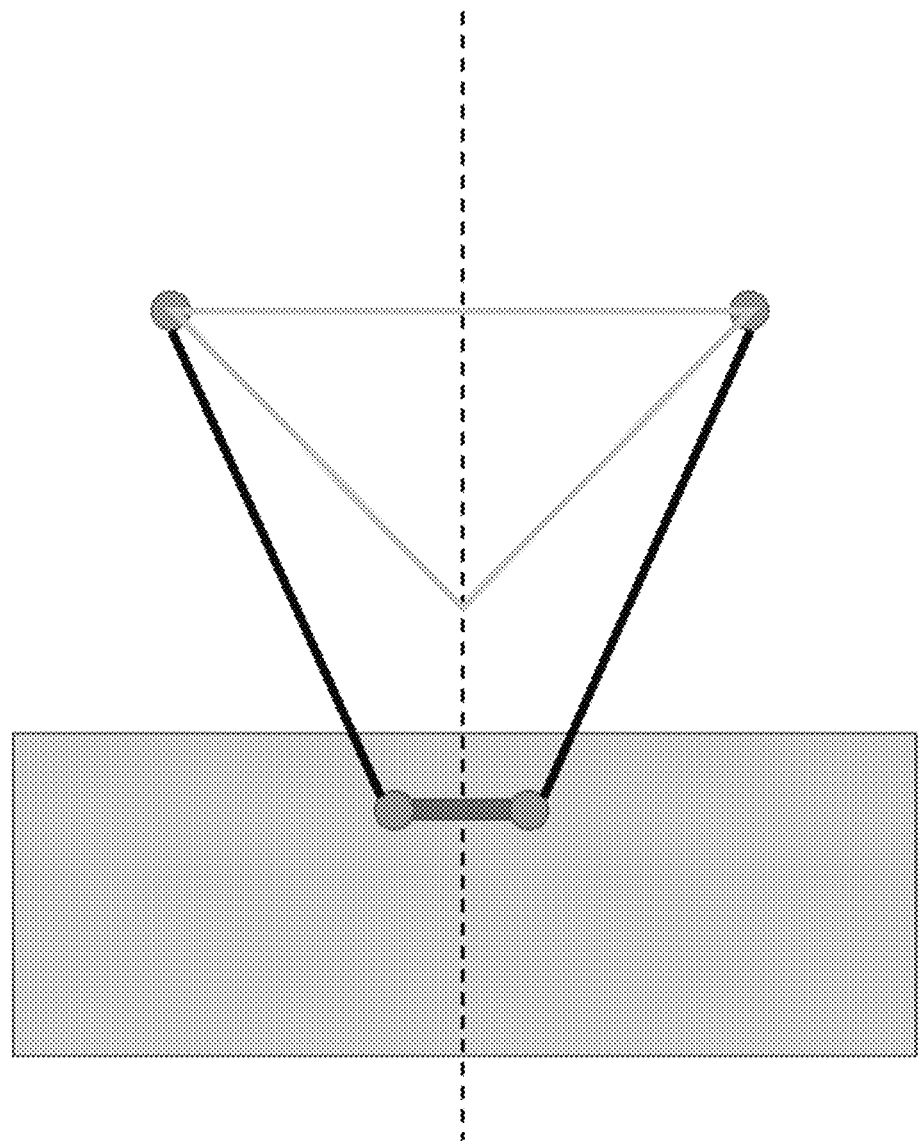
Figure 11E:
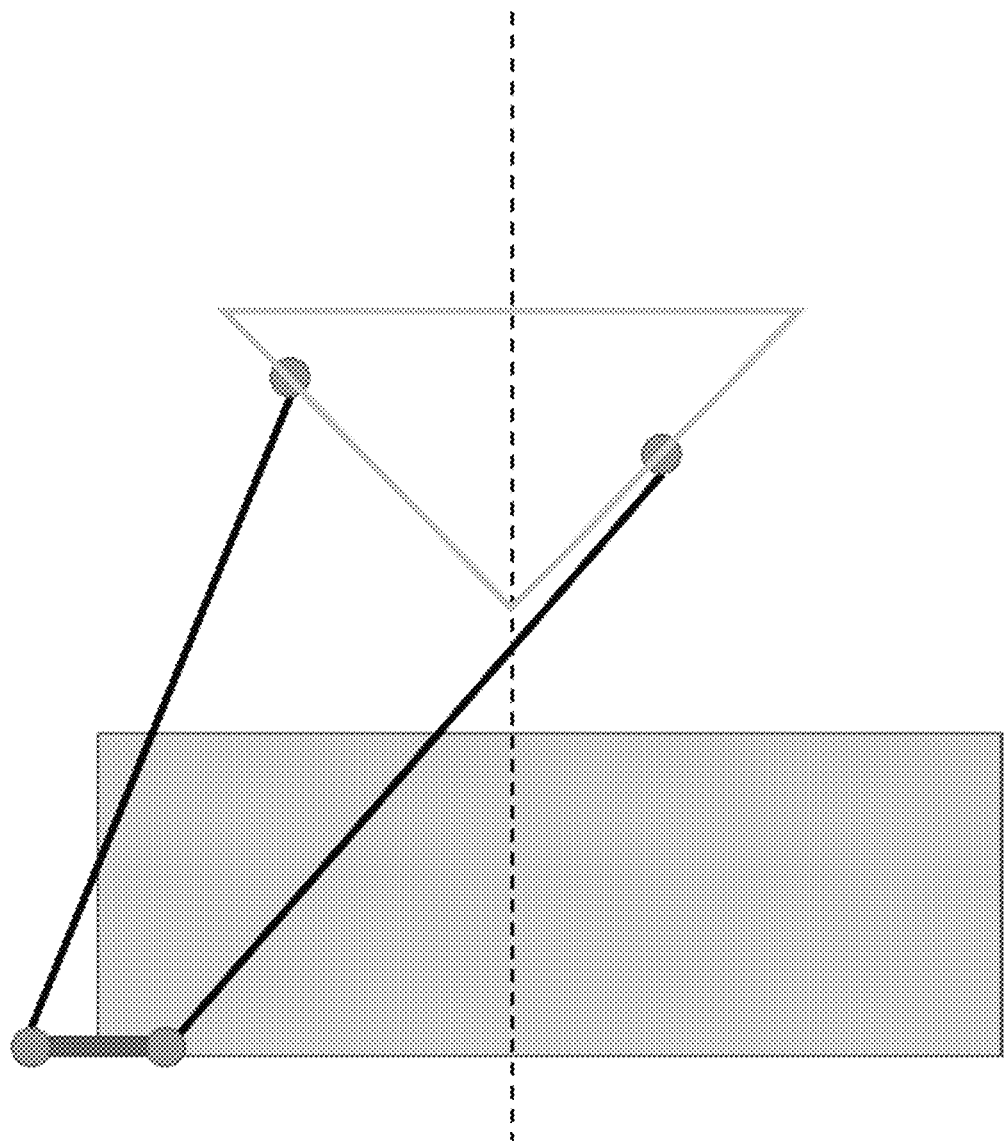
Figure 11F:
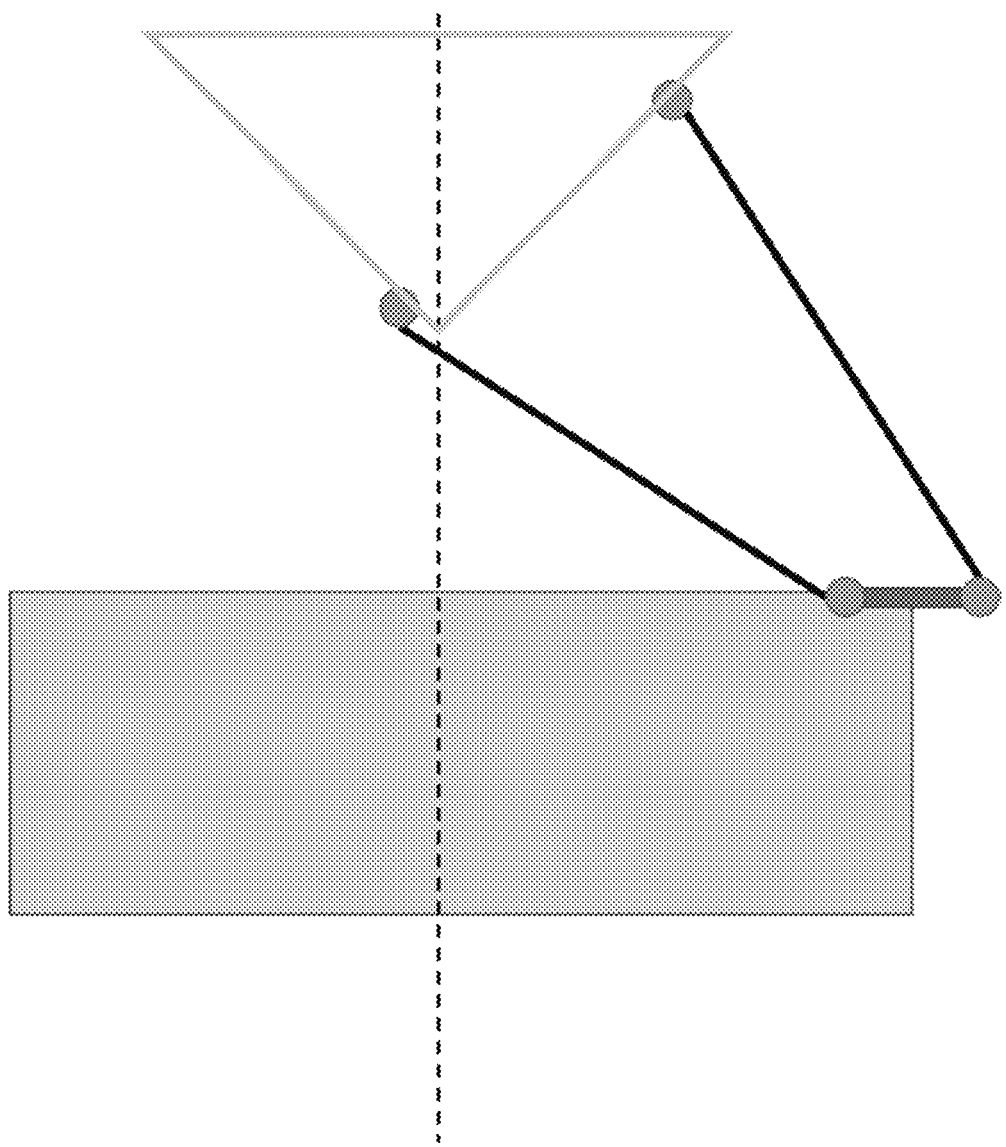

FIGS. 11A-F show the schematic drawings of some embodiments of alternative actuation methods. In particular, FIGS. 11A-C illustrate the actuation methods using rotational joints and FIGS. 11D-11F illustrate the actuation method using a linear motor. There are trade-offs that need to be considered. Rotational joints are highly space-efficient and can drive the systems moving relatively fast, but they cannot provide steady positioning due to the mechanical structure limits and motor limits. Linear actuation, such as Ball screw tables, can provide high precision and high revolution but they can hardly reach high speed manipulation. In FIG. 4, $\varphi$ is used to describe the relationship between sliding track and links and define the singularity condition correspondingly. When taking rotational joints into consideration, the critical angles that define the singularity condition are $\gamma_1$ and $\gamma_2$ as shown in FIG. 11C. The critical angles are $\gamma_1'$ and $\gamma_2'$ in the situation shown in FIG. 11F, if linear actuation is utilized correspondingly. Variations of the parallel actuation methods do change the overall design pipeline of the robotic structures and all parallel actuation methods are valid as long as they can fulfill the requirements of the application.

Figure 12A:
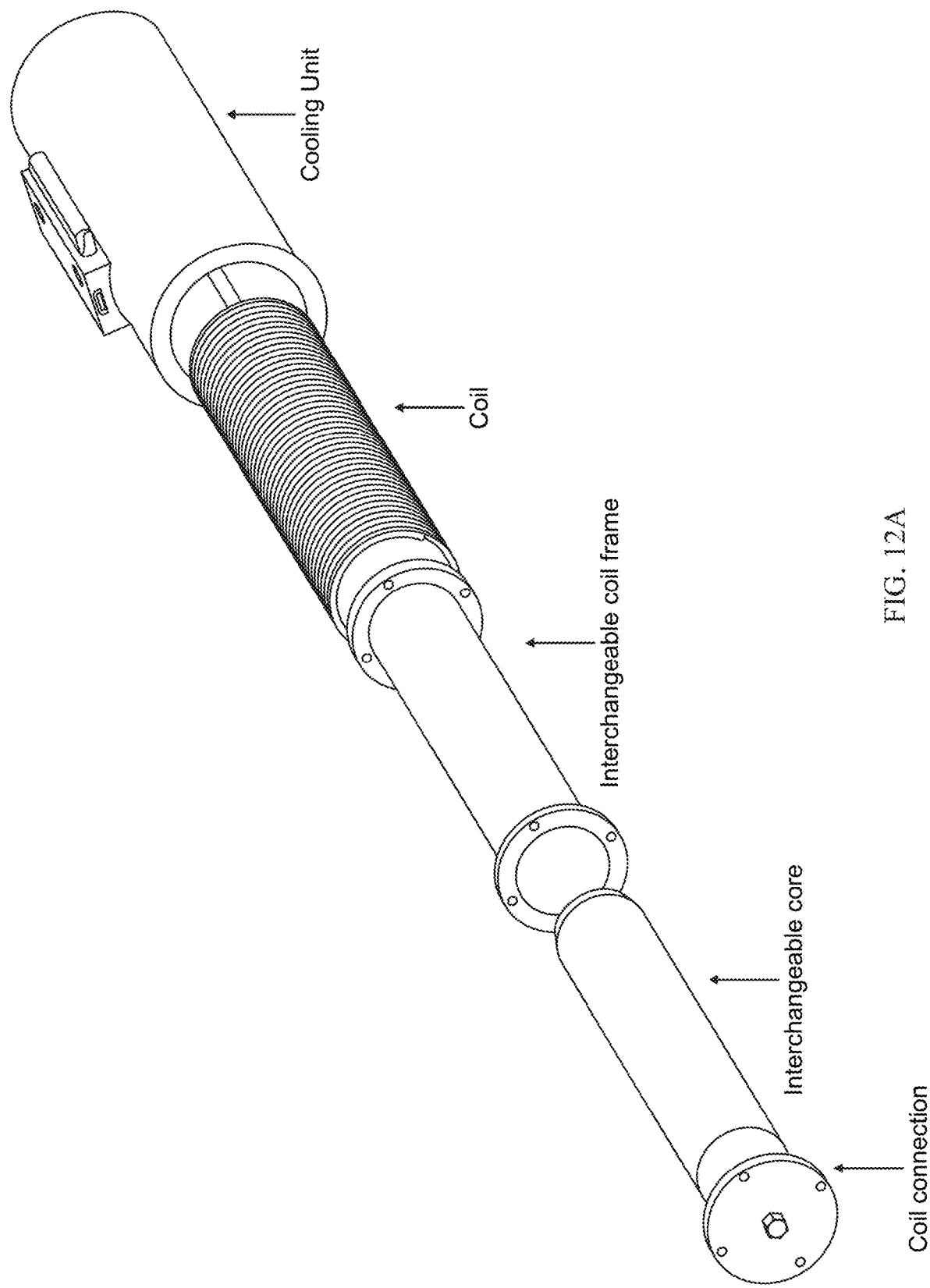
FIGS. 12A-12D are schematic representations illustrating the interchangeable coil assembly and coil connection methods, according to an embodiment of the subject invention.
Figure 12B:
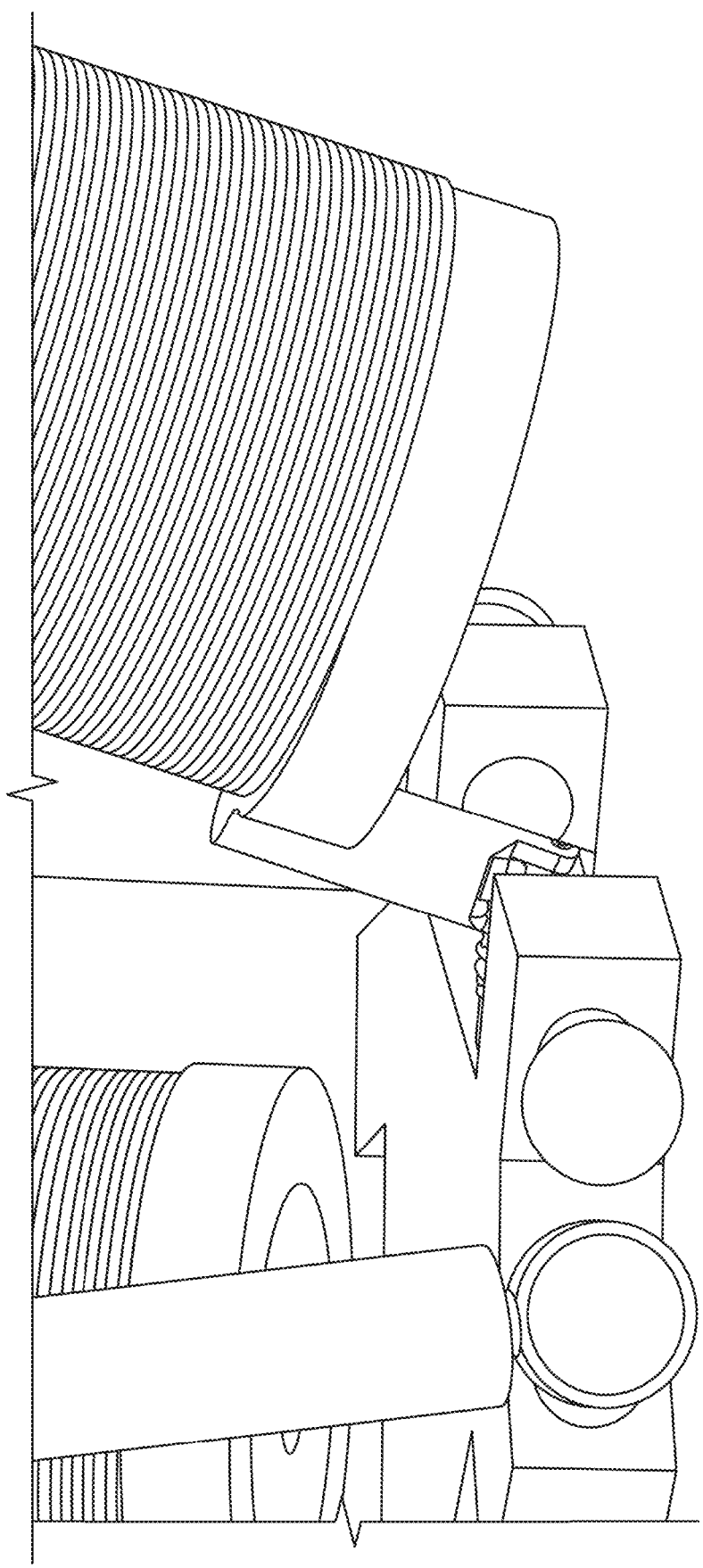
Figure 12C:
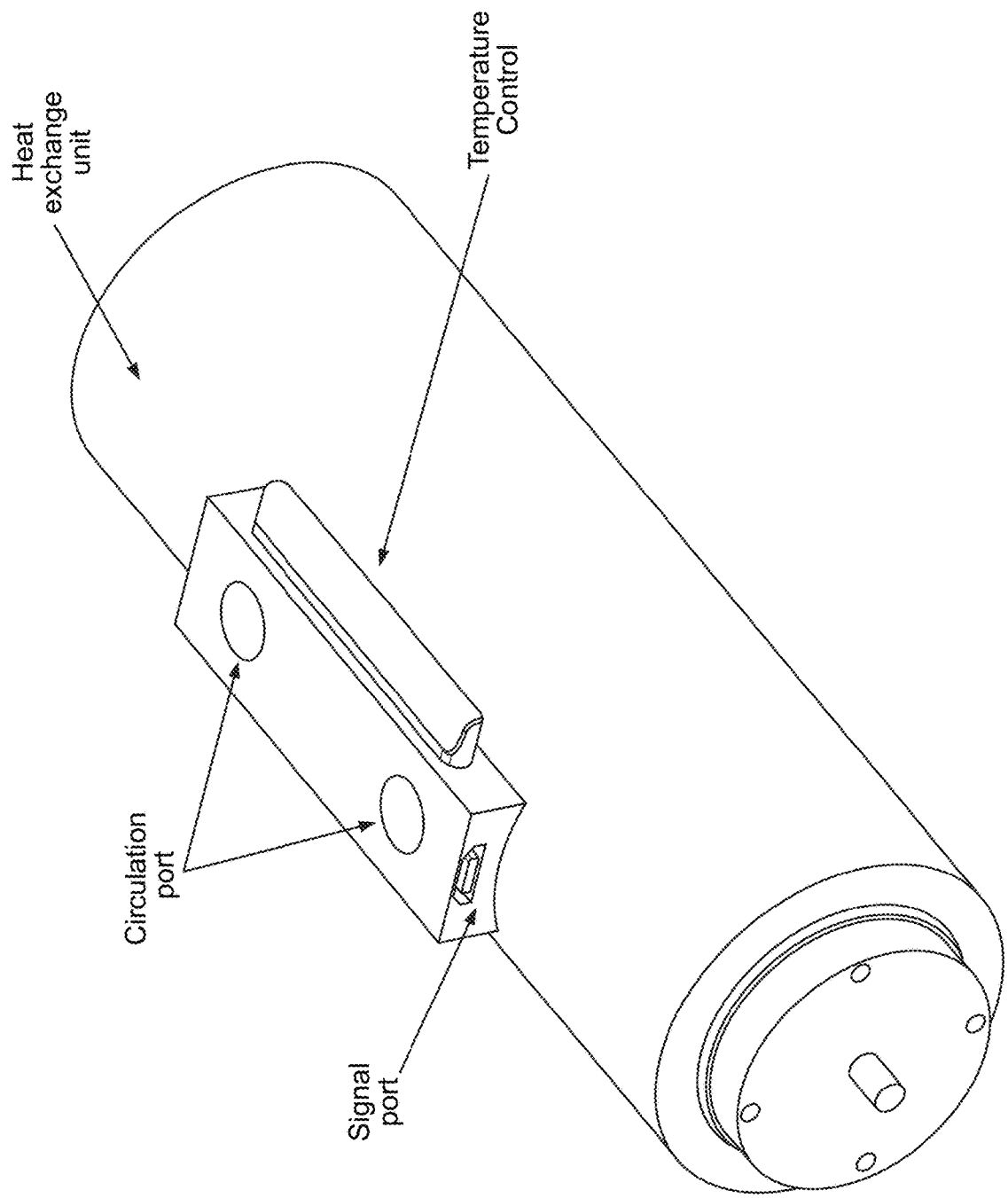
Figure 12D:
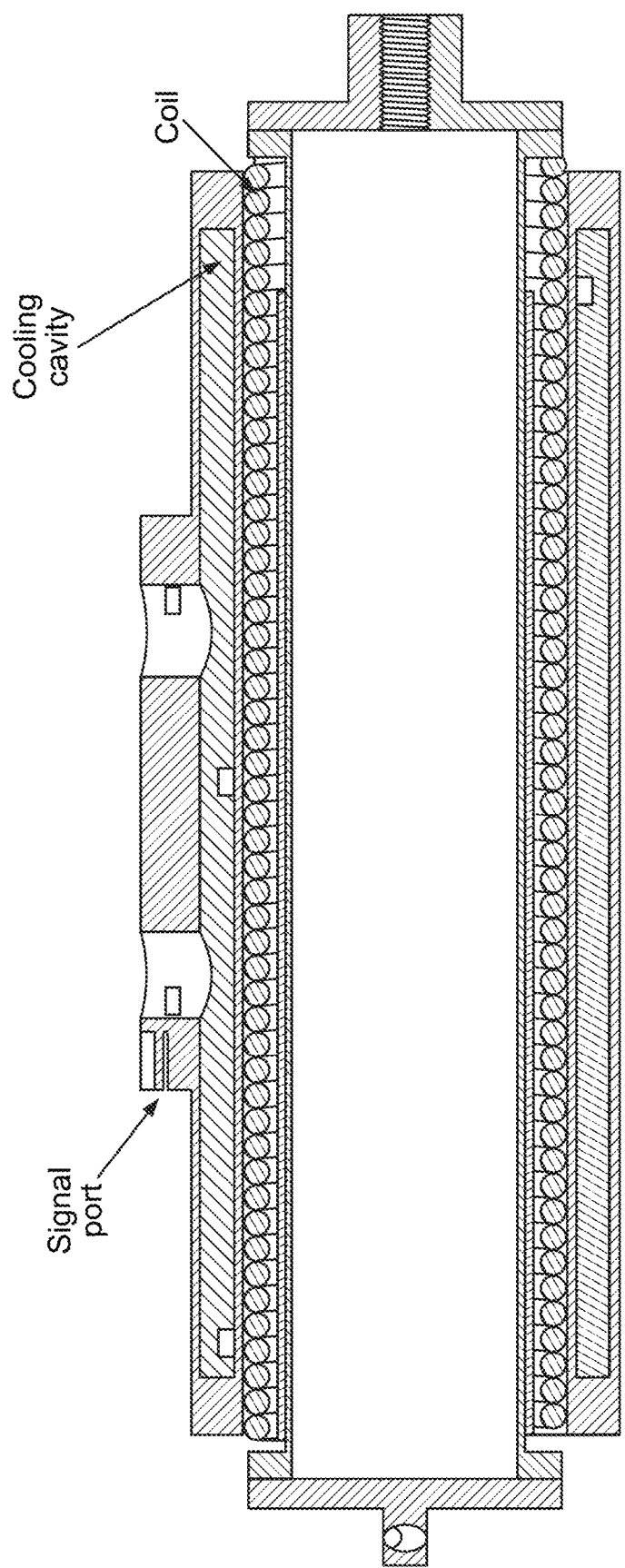

FIGS. 12A-12D show schematic drawings of the interchangeable coil assembly. In particular, FIG. 12A shows the exploded view of the coil assembly. A complete coil assembly includes a connection part, a core, a coil frame, a coil and a cooling unit. Connection can be flanges or screw holes as shown in FIG. 12A. If an extruded core tip is applied, side connection as shown in FIG. 12B can be used. The side connection method can give more space for the extruded core tip and decrease the distance between core and the controlled object. A core can be inserted into the coil frame and therefore different core material can be selected. The coil frame is a socket with two side flange connection. The utilization of the frame can decouple the core and the coil which enables better flexibility. Due to the modulated design, any part of the coil assembly can be substituted when the coil assembly needs maintenance. As shown in FIGS. 12C-12D, the cooling unit comprises two parts: the heat exchange unit and the temperature control unit. The heat exchange unit has a cooling cavity for circulation of the coolant and it is made of high thermal conductivity material. There are sensors installed in the cooling cavity which is shown as orange blocks in FIG. 12D, monitoring the temperature change. They feedback the temperature signal through signal ports to the host computer and achieve close loop control of the coil temperature. The cooling control unit regulates the cooling effect and thus keeps the coil in a reliable working temperature window. Overheating causes device failure and hazardous incidents. The cooling system can elongate continuous working time of the system and protect the user and the operator from potential harms.

Figure 13A:
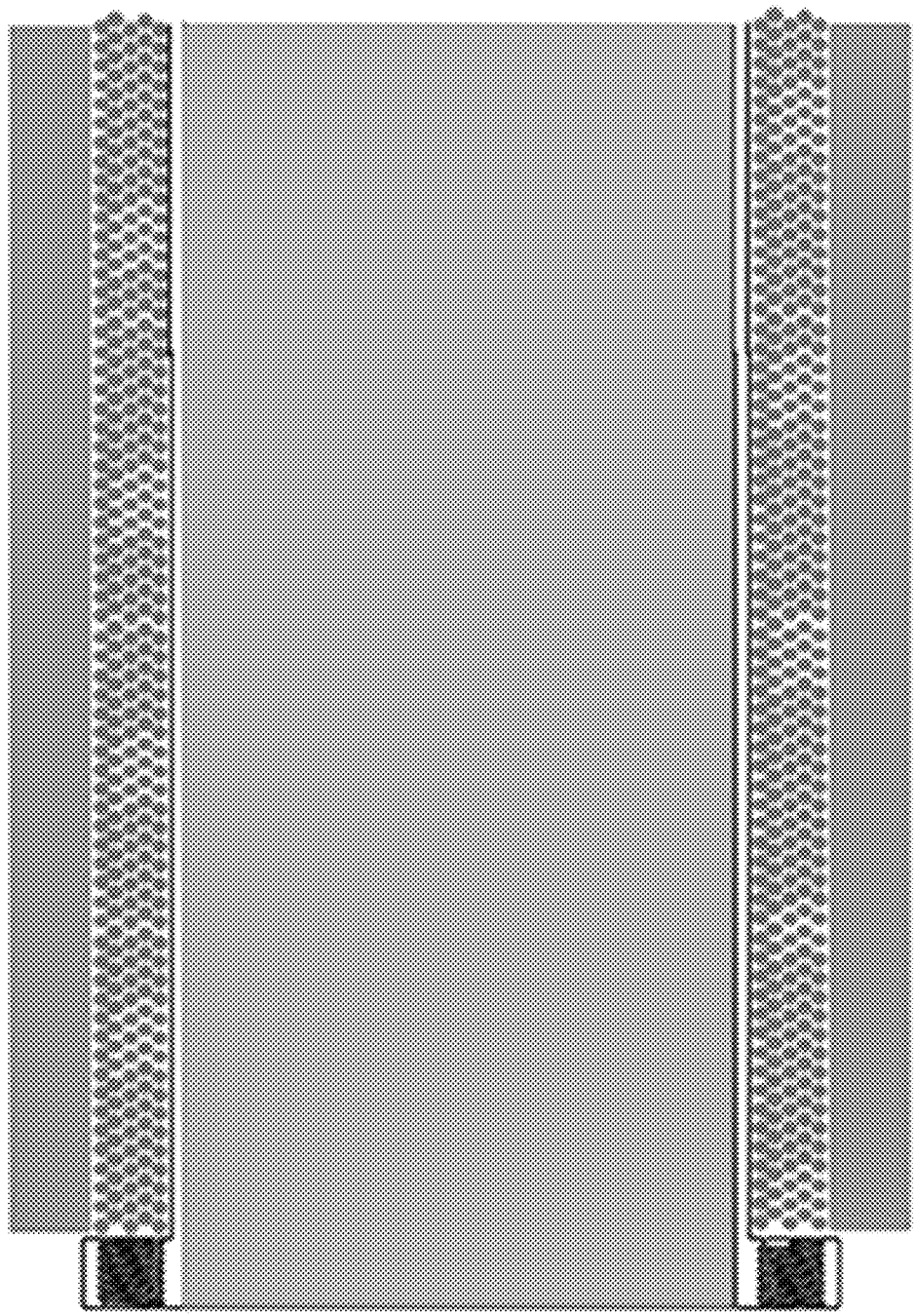
FIGS. 13A-13D are schematic representations illustrating various coil tip shapes, according to an embodiment of the subject invention.
Figure 13B:
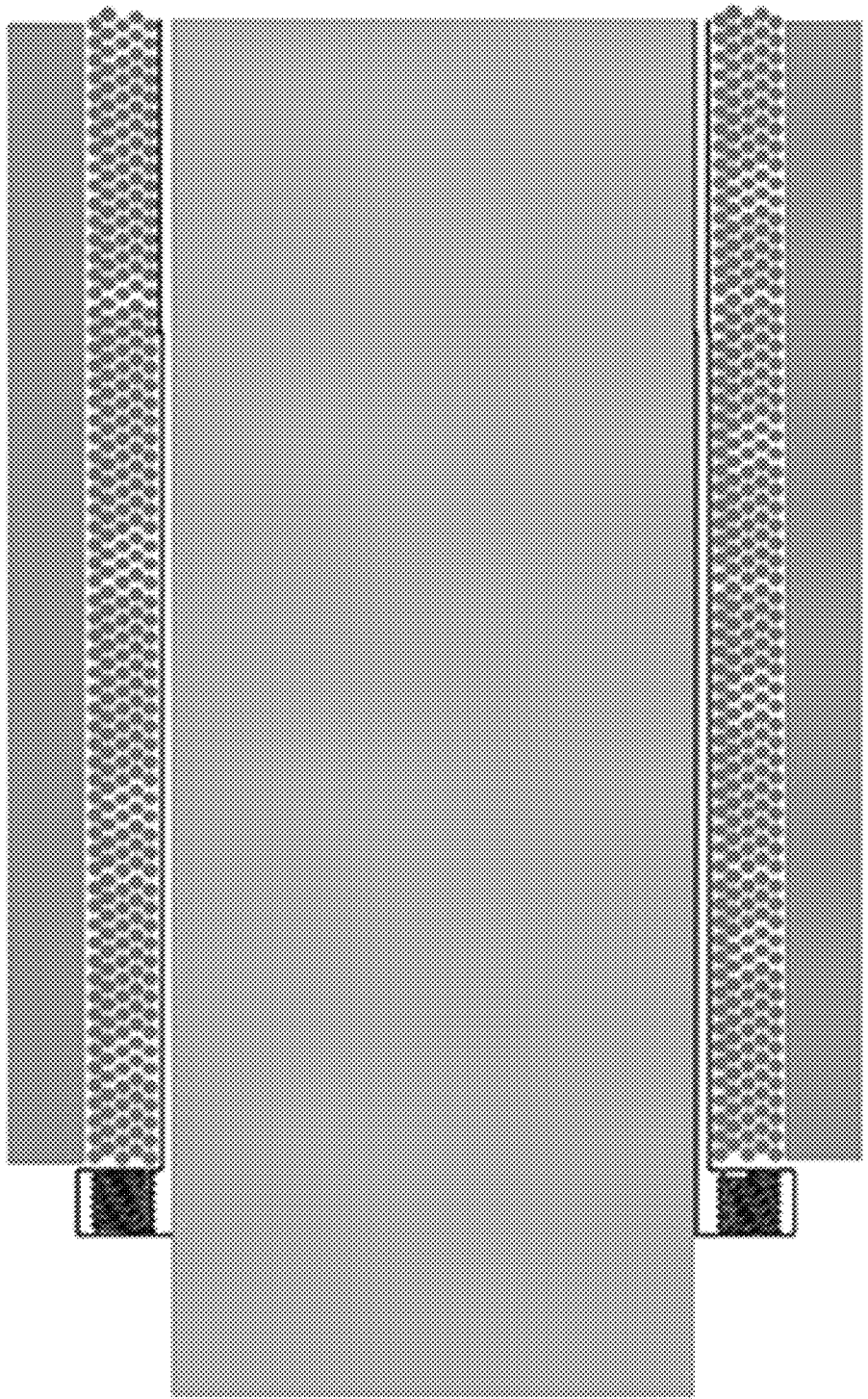
Figure 13C:
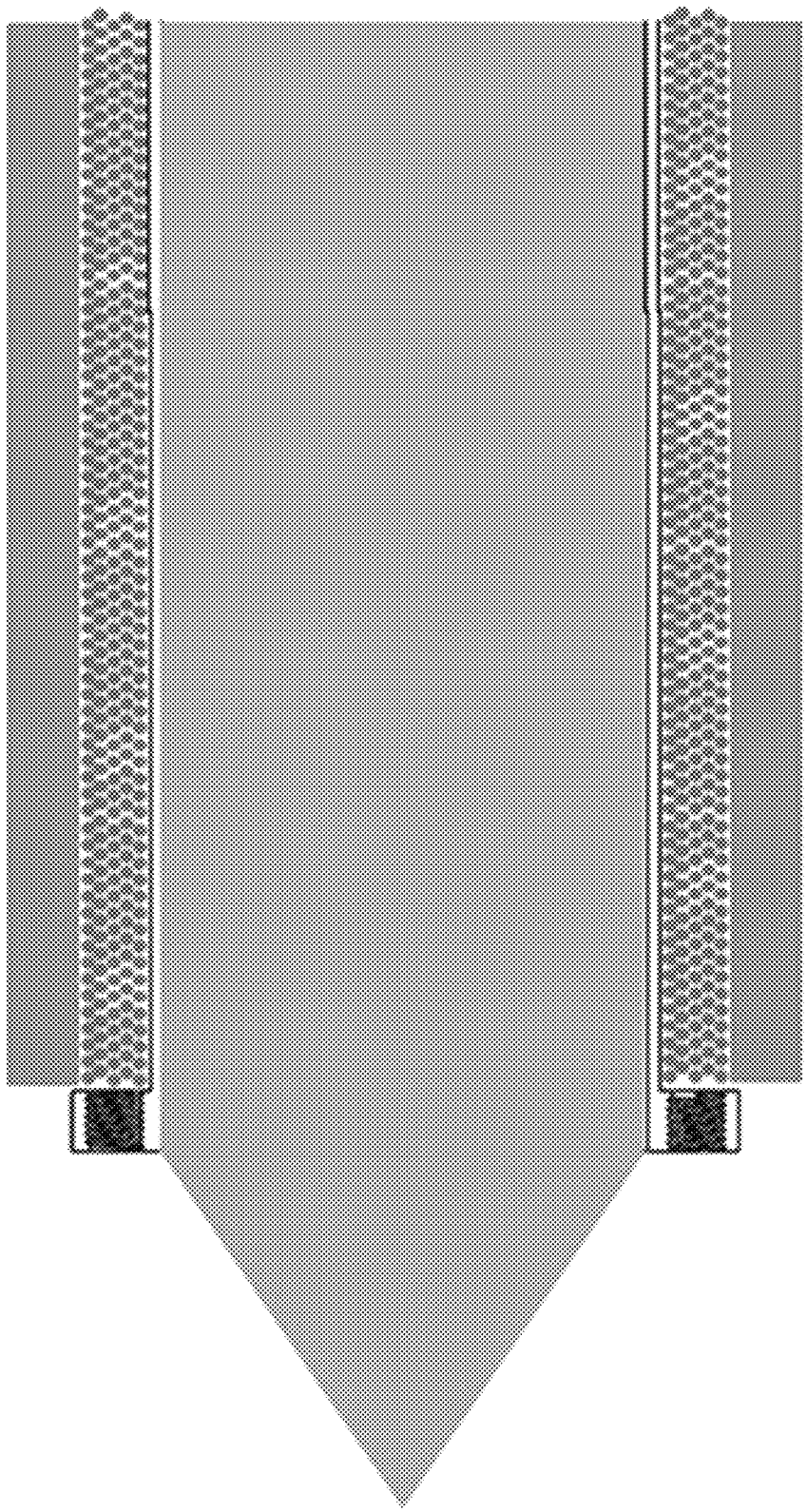
Figure 13D:
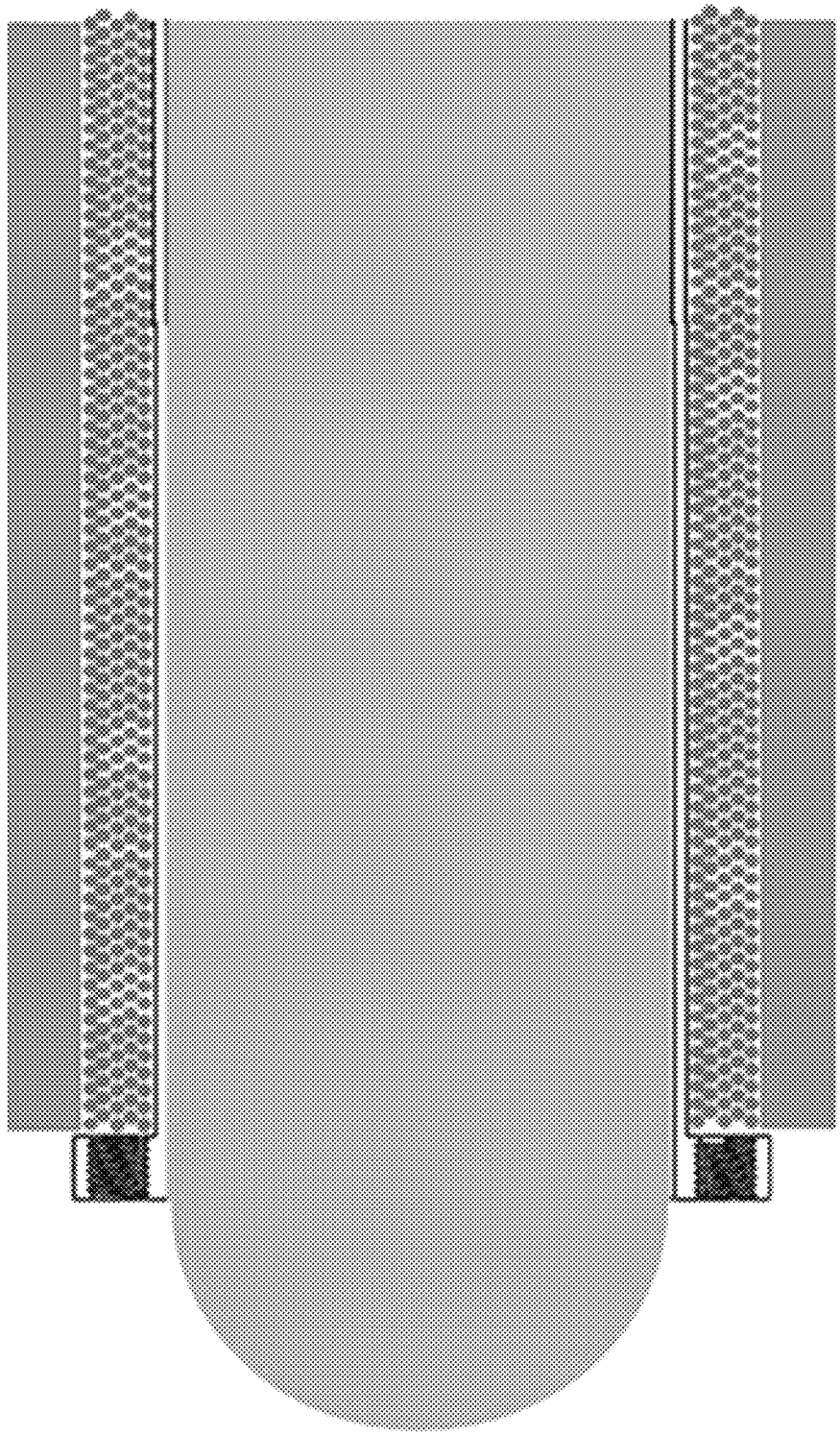

FIGS. 13A-13D show certain alternative core tip shapes. Different core tip shapes generate different kinds of magnetic fields, each shape having its own advantages. Ordinary tip shape as shown in FIG. 13A generates medium strong magnetic field in medium range. Extruded shape shown in FIG. 13B gives a stronger magnetic strength in a shorter range and the magnetic field degrades faster. Cone tip as shown in FIG. 13C can greatly concentrate very strong magnetic field in a small area. The half-sphere tip as shown in FIG. 13D can generate more uniform magnetic field. The core tip can have many shapes which are not limited to the examples shown in the FIGS. 13A-13D. Due to the interchangeable design of the coil assembly, core tip shape can be adjusted by changing the core. The flexibility helps the system to meet various requirements.

Figure 14A:
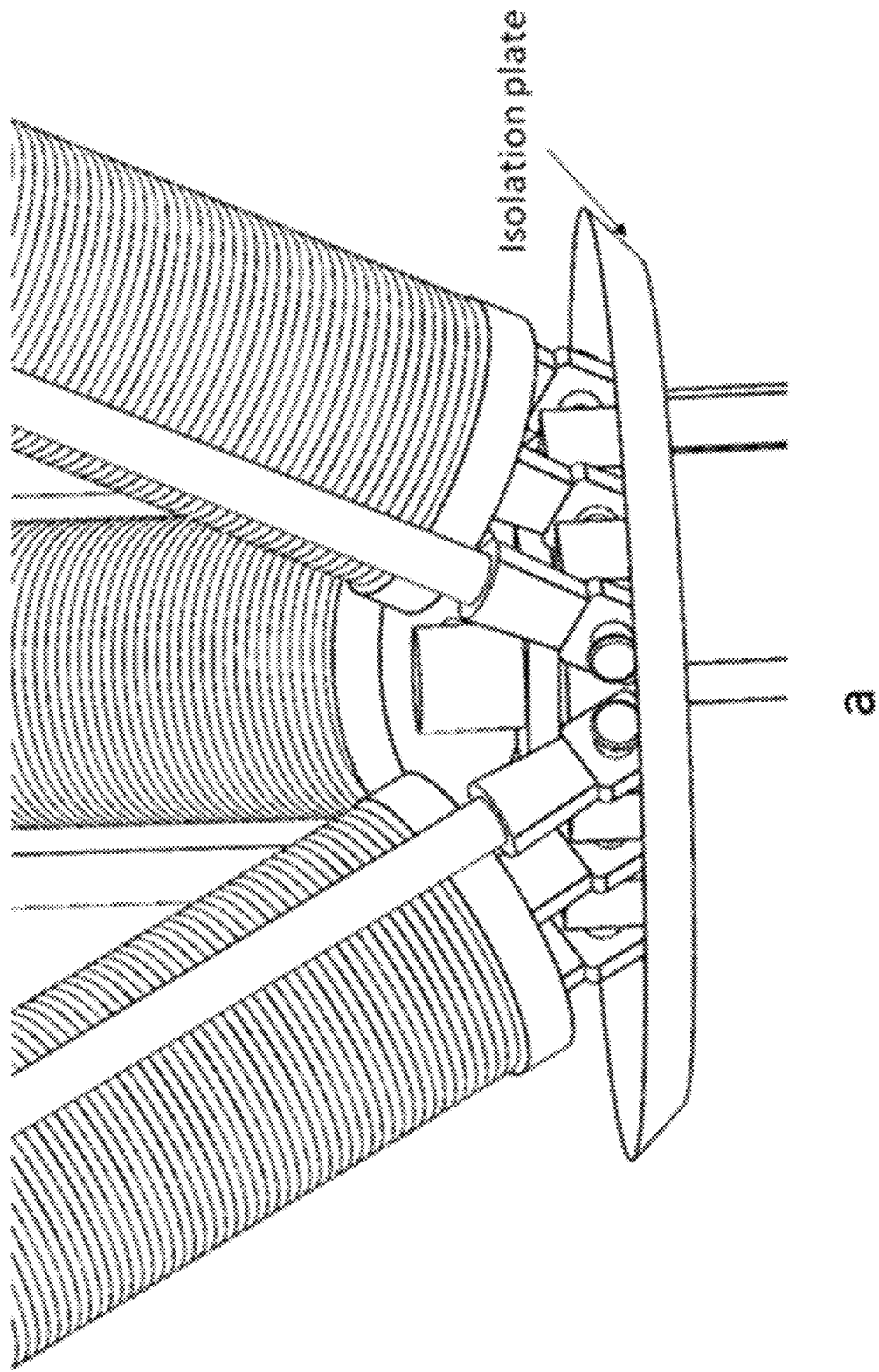
FIGS. 14A-14B are schematic representations illustrating an isolation plate, according to an embodiment of the subject invention.
Figure 14B:
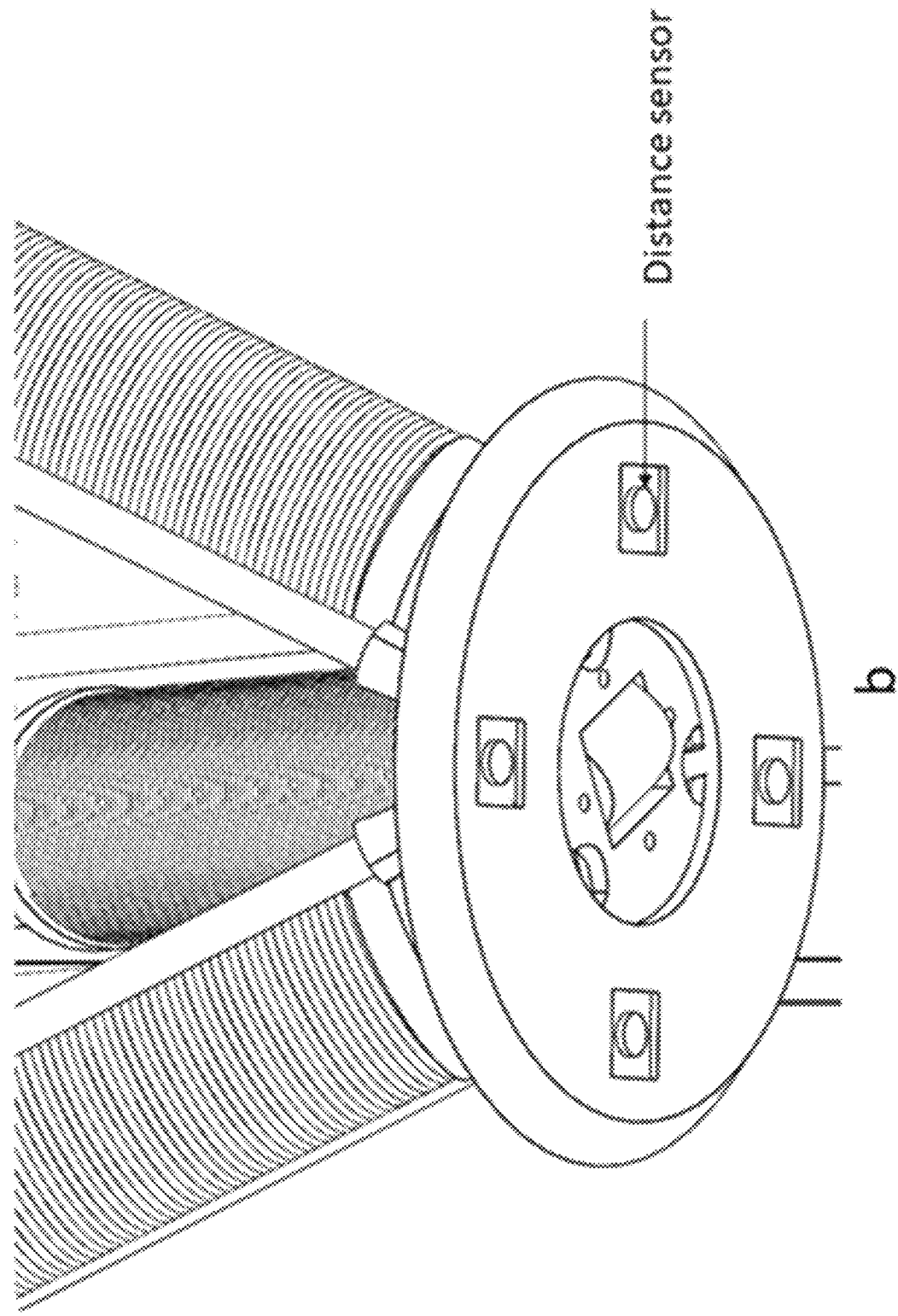

FIGS. 14A-14B show the schematic drawing of an isolation plate for inhibiting heat and electricity. The distance sensors can send signals back to the host computer to indicate the distance between the isolation plate and the body surface such that a method can be implemented to inhibit collision between the system and the body. The body in which the system controls the magnetic objects can be a human body or an animal body. The isolation plate helps minimize the potential harm that the system can do to the body.

The present invention provides a magnetic manipulation and navigation system utilizing parallel-structured mobile electromagnetic coils for moving and navigating magnetic devices in a body.

The parallel mechanism precisely positions the electromagnetic coils to targeted locations and a control unit is configured to regulate the currents in the electromagnetic coils. The magnetic manipulation and navigation system can manipulate a magnetic device in a large 3D working area in the vicinity of the body with a combination of robotic structure position control and electromagnetic coil current control, inhibiting the use of huge electromagnetic coils and superconducting electromagnets.

At least three electromagnets with soft iron cores are installed on the parallel-structured linkage and these electromagnets connect to one another through a coil-end joint plate. The electromagnetic coils can move to any location by actuating the parallel mechanism and the control unit can adapt the coil currents to drive the electromagnetic coils to generate specific dynamic magnetic field. Because of the movement capability of the coils, a large 3D workspace is promised while the coils can be kept in the vicinity of the controlled devices so that the scalability problems of coils are inhibited.

Owing to the special structure of the parallel mechanism, the coils can be integrated as part of the robot structure. On one hand, the electromagnetic coils that are compactly structured by the parallel links have high stiffness when the parallel mechanism linkage is held in static position. On the other hand, the parallel mechanism-structured linkages that connect each electromagnetic coil can be actuated to move the electromagnetic coils to desired locations in the vicinity of the body where the magnetic device locates.

Furthermore, the electromagnetic coils can move along a preferred trajectory and the current running in the coils can be controlled to generate desired magnetic fields when the magnetic manipulation and navigation system is moving a magnetic element through the body.

Moreover, the workspace can be easily enlarged without requirements to upgrade the size of the coils and the ratio between the volume of effective workspace and the volume of the whole system is much higher than the existing electromagnetic manipulation systems.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. US 20120281330A1
2. U.S. Pat. No. 7,073,513B2
3. US 20160143514A1
4. U.S. Pat. No. 9,445,711B2
5. US 20190104994A1
6. U.S. Pat. No. 6,311,082B1
7. U.S. Ser. No. 10/004,566B2
8. US 20150380140A1
9. EP 2995240A1
10. U.S. Pat. No. 8,452,377B2
11. US 20170150874A1
12. US 20150230810A1
13. U.S. Pat. No. 6,459,924B1
14. U.S. Pat. No. 6,975,197B2
15. US 20140066752A1

The invention claimed is:

1. A magnetic manipulation system having mobile coils for moving and navigating a magnetic device in a body, comprising:
   a robotic parallel mechanism comprising at least three electromagnets and at least three electromagnetic coils coupled to the at least three electromagnets, respectively, wherein the electromagnetic coils are actuated to keep the electromagnets in static conditions or move the electromagnets along a desired trajectory;
   a current control unit supplying currents to the electromagnetic coils, the electromagnetic coils having soft iron cores, wherein the currents supplied by the control unit are configured to generate a dynamic magnetic field in a linear region of each soft iron core, wherein the current control unit and the robotic parallel mechanism are configured to generate desired dynamic magnetic fields in desired positions within a workspace to control a magnetic device; and
   a three-dimensional (3D) position sensor configured for performing a close loop control of the robotic parallel mechanism.

2. The magnetic manipulation system of claim 1, further comprising a coil-end joint plate, actuation units, and structural linkages that connect the coil-end joint plate to the robotic parallel mechanism.

3. The magnetic manipulation system of claim 2, wherein the coil-end joint plate has a plurality of sides corresponding to a plurality of branches of each electromagnetic coil, and wherein instruments are mounted on the coil-end joint plate and the coil-end joint plate is connected to a lower end of each electromagnetic coil.

4. The magnetic manipulation system of claim 2, wherein the robotic parallel mechanism is an actuation mechanism having K branches including linear actuation mechanisms and rotational actuation mechanisms, wherein K is an integer greater than zero, and wherein the rotational actuation mechanisms include motors and gears, motors and belts, or motors and linkages, and wherein the linear actuation mechanisms include ball screw tables, sliding tracks, and pneumatic actuation.

5. The magnetic manipulation system of claim 2, wherein the robotic parallel mechanism is made of low magnetic permittivity materials including aluminum and 304 steel.

6. The magnetic manipulation system of claim 2, wherein a position of a center of the coil-end joint plate has a deterministic relationship with actuator positions of the robotic parallel mechanism while an orientation of the coil-end joint plate is constrained by the robotic parallel mechanisms to be invariant.

7. The magnetic manipulation system of claim 2, the coil-end joint plate is configured to install one or more instruments selected from 3D ultrasonic probes, 3D magnetic sensors or stereo cameras, the 3D ultrasonic probes, the 3D magnetic sensors, and the stereo cameras being modulated and interchangeable.

8. The magnetic manipulation system of claim 7, wherein a 3D location method is configured to conduct close loop control of a plurality of magnetic objects, and wherein the 3D location method includes one or more selected from ultrasonic imaging, magnetic localization, and vision-based localization method, depending on the instruments installed on the coil-end joint plate.

9. The magnetic manipulation system of claim 2, wherein the electromagnetic coils are connected to the coil-end joint plate by universal joints, and wherein the electromagnetic coils move and are aligned with the structural linkages.

10. The magnetic manipulation system of claim 2, further comprising an isolation plate attached to the coil-end joint plate for controlling a distance between the magnetic manipulation system and the body that includes magnetically controlled objects and integrates distance sensors and temperature sensors to inhibit body collision and overheating.

\* \* \* \* \*